(12) United States Patent
Gong et al.

(10) Patent No.: US 10,702,269 B2
(45) Date of Patent: Jul. 7, 2020

(54) SURGICAL STAPLING DEVICES

(71) Applicant: Covidien LP, Mansfield, MA (US)

(72) Inventors: Damao Gong, Shanghai (CN); Xiliang Zhang, Shanghai (CN); Yuandong Tan, Shanghai (CN)

(73) Assignee: Covidien LP, Mansfield, MA (US)

( * ) Notice: Subject to any disclaimer, the term of this patent is extended or adjusted under 35 U.S.C. 154(b) by 313 days.

(21) Appl. No.: 15/535,076

(22) PCT Filed: Dec. 25, 2014

(86) PCT No.: PCT/CN2014/094918
§ 371 (c)(1),
(2) Date: Jun. 12, 2017

(87) PCT Pub. No.: WO2016/101206
PCT Pub. Date: Jun. 30, 2016

(65) Prior Publication Data
US 2017/0340324 A1 Nov. 30, 2017

(51) Int. Cl.
*A61B 17/072* (2006.01)
*A61B 17/32* (2006.01)
(52) U.S. Cl.
CPC .......... *A61B 17/072* (2013.01); *A61B 17/32* (2013.01); *A61B 2017/07271* (2013.01)
(58) Field of Classification Search
CPC .... A61B 17/115; A61B 17/068; A61B 17/072
See application file for complete search history.

(56) References Cited

U.S. PATENT DOCUMENTS

| 1,158,111 | A | 10/1915 | Ahlheim |
| 2,891,250 | A | 6/1959 | Hirata |
| 3,080,564 | A | 3/1963 | Strekopitov et al. |
| 3,252,643 | A | 5/1966 | Strekopov et al. |
| 3,269,630 | A | 8/1966 | Fleischer |

(Continued)

FOREIGN PATENT DOCUMENTS

| CN | 1669534 A | 9/2005 |
| CN | 202604932 U | 12/2012 |

(Continued)

OTHER PUBLICATIONS

International Search Report for PCT/CN2014/094918 date of completion is Sep. 15, 2015 (2 pages).

(Continued)

*Primary Examiner* — Stephen F. Gerrity
*Assistant Examiner* — Joshua G Kotis
(74) *Attorney, Agent, or Firm* — Carter, DeLuca & Farrell LLP

(57) ABSTRACT

A surgical stapling device (10) includes a frame (36), a pusher (105), a clamping plate assembly (110), a holder (180), and a stapling plate (220). The pusher (105) is movable in relation to the frame (36) between a retracted position and an advanced position. The pusher (105) is operatively associated with the holder (180), the clamping plate assembly (110), and the stapling plate (220) such that movement of the pusher (105) between the retracted and the advanced positions effects movement of the (105), the clamping plate assembly (110), and the stapling plate (220) to one of their respective retracted or advanced positions.

22 Claims, 16 Drawing Sheets

(56) References Cited

U.S. PATENT DOCUMENTS

| | | | |
|---|---|---|---|
| 3,275,211 | A | 9/1966 | Hirsch et al. |
| 3,315,863 | A | 4/1967 | O'Dea |
| 3,494,533 | A | 2/1970 | Green et al. |
| 3,589,589 | A | 6/1971 | Akopov |
| 3,692,224 | A | 9/1972 | Astafiev et al. |
| 3,795,034 | A | 3/1974 | Strekopytov et al. |
| 3,822,818 | A | 7/1974 | Strekopytov et al. |
| 3,935,981 | A | 2/1976 | Akopov et al. |
| 3,949,923 | A | 4/1976 | Akopov et al. |
| 4,047,654 | A | 9/1977 | Alvarado |
| 4,216,891 | A | 8/1980 | Behlke |
| 4,244,372 | A | 1/1981 | Kapitanov et al. |
| 4,296,881 | A | 10/1981 | Lee |
| 4,305,539 | A | 12/1981 | Korolkov et al. |
| 4,354,628 | A | 10/1982 | Green |
| 4,378,901 | A | 4/1983 | Akopov et al. |
| 4,383,634 | A | 5/1983 | Green |
| 4,402,444 | A | 9/1983 | Green |
| 4,415,112 | A | 11/1983 | Green |
| D273,513 | S | 4/1984 | Spreckelmeier |
| 4,442,964 | A | 4/1984 | Becht |
| 4,470,533 | A | 9/1984 | Schuler |
| 4,475,679 | A | 10/1984 | Fleury, Jr. |
| 4,485,811 | A | 12/1984 | Chernousov et al. |
| 4,506,670 | A | 3/1985 | Crossley |
| 4,506,671 | A | 3/1985 | Green |
| 4,508,253 | A | 4/1985 | Green |
| 4,522,327 | A | 6/1985 | Korthoff et al. |
| 4,527,724 | A | 7/1985 | Chow et al. |
| 4,530,453 | A | 7/1985 | Green |
| 4,550,870 | A | 11/1985 | Krumme et al. |
| 4,566,620 | A | 1/1986 | Green et al. |
| 4,568,009 | A | 2/1986 | Green |
| 4,573,622 | A | 3/1986 | Green et al. |
| 4,580,712 | A | 4/1986 | Green |
| 4,585,153 | A | 4/1986 | Failla et al. |
| 4,589,582 | A | 5/1986 | Bilotti |
| 4,602,634 | A | 7/1986 | Barkley |
| 4,605,001 | A | 8/1986 | Rothfuss et al. |
| 4,605,004 | A | 8/1986 | Di Giovanni et al. |
| 4,606,344 | A | 8/1986 | Di Giovanni |
| 4,606,345 | A | 8/1986 | Dorband et al. |
| 4,607,636 | A | 8/1986 | Kula et al. |
| 4,612,933 | A | 9/1986 | Brinkerhoff et al. |
| 4,617,928 | A | 10/1986 | Alfranca |
| 4,632,290 | A | 12/1986 | Green et al. |
| 4,665,916 | A | 5/1987 | Green |
| 4,684,051 | A | 8/1987 | Akopov et al. |
| 4,714,187 | A | 12/1987 | Green |
| 4,715,520 | A | 12/1987 | Roehr, Jr. et al. |
| 4,728,020 | A | 3/1988 | Green et al. |
| 4,767,044 | A | 8/1988 | Green |
| 4,788,978 | A | 12/1988 | Strekopytov et al. |
| 4,802,614 | A | 2/1989 | Green et al. |
| 4,805,823 | A | 2/1989 | Rothfuss |
| 4,819,853 | A | 4/1989 | Green |
| 4,848,637 | A | 7/1989 | Pruitt |
| 4,869,414 | A | 9/1989 | Green et al. |
| 4,881,544 | A | 11/1989 | Green et al. |
| 4,881,545 | A | 11/1989 | Isaacs et al. |
| 4,915,100 | A | 4/1990 | Green |
| 4,930,503 | A | 6/1990 | Pruitt |
| 4,938,408 | A | 7/1990 | Bedi et al. |
| 4,941,623 | A | 7/1990 | Pruitt |
| 4,951,861 | A | 8/1990 | Schulze et al. |
| 4,964,559 | A | 10/1990 | Deniega et al. |
| 5,005,754 | A | 4/1991 | Van Overloop |
| 5,018,657 | A | 5/1991 | Pedlick et al. |
| 5,071,052 | A | 12/1991 | Rodak et al. |
| 5,100,042 | A | 3/1992 | Gravener et al. |
| 5,116,349 | A | 5/1992 | Aranyi |
| 5,137,198 | A | 8/1992 | Nobis et al. |
| 5,172,845 | A | 12/1992 | Tejeiro |
| 5,190,203 | A | 3/1993 | Rodak |
| 5,219,111 | A | 6/1993 | Bilotti et al. |
| 5,240,163 | A | 8/1993 | Stein et al. |
| 5,344,060 | A | 9/1994 | Gravener et al. |
| 5,368,599 | A | 11/1994 | Hirsch et al. |
| 5,405,073 | A | 4/1995 | Porter |
| 5,413,267 | A | 5/1995 | Solyntjes et al. |
| 5,439,155 | A | 8/1995 | Viola |
| 5,452,836 | A | 9/1995 | Huitema et al. |
| 5,458,279 | A | 10/1995 | Plyley |
| 5,462,215 | A | 10/1995 | Viola et al. |
| 5,464,144 | A | 11/1995 | Guy et al. |
| 5,465,894 | A | 11/1995 | Clark et al. |
| 5,470,006 | A | 11/1995 | Rodak |
| 5,470,008 | A | 11/1995 | Rodak |
| 5,470,009 | A | 11/1995 | Rodak |
| 5,497,934 | A | 3/1996 | Brady et al. |
| 5,503,320 | A | 4/1996 | Webster et al. |
| 5,509,596 | A | 4/1996 | Green et al. |
| 5,542,594 | A | 8/1996 | McKean et al. |
| 5,547,117 | A | 8/1996 | Hamblin et al. |
| 5,558,266 | A | 9/1996 | Green et al. |
| 5,579,978 | A | 12/1996 | Green et al. |
| 5,580,067 | A | 12/1996 | Hamblin et al. |
| 5,603,443 | A | 2/1997 | Clark et al. |
| 5,605,272 | A | 2/1997 | Witt et al. |
| 5,605,273 | A | 2/1997 | Hamblin et al. |
| 5,607,094 | A | 3/1997 | Clark et al. |
| 5,615,820 | A | 4/1997 | Viola |
| 5,641,111 | A | 6/1997 | Ahrens et al. |
| 5,678,748 | A | 10/1997 | Plyley et al. |
| 5,697,543 | A | 12/1997 | Burdorff |
| 5,706,997 | A | 1/1998 | Green et al. |
| 5,706,998 | A | 1/1998 | Plyley et al. |
| 5,732,871 | A | 3/1998 | Clark et al. |
| 5,735,445 | A | 4/1998 | Vidal et al. |
| 5,794,834 | A | 8/1998 | Hamblin et al. |
| 5,810,240 | A | 9/1998 | Robertson |
| 5,855,311 | A | 1/1999 | Hamblin et al. |
| 5,878,937 | A | 3/1999 | Green et al. |
| 5,893,506 | A | 4/1999 | Powell |
| 5,894,979 | A | 4/1999 | Powell |
| 5,964,394 | A | 10/1999 | Robertson |
| 6,045,560 | A | 4/2000 | McKean et al. |
| 6,638,285 | B2 | 10/2003 | Gabbay |
| 6,805,273 | B2 | 10/2004 | Bilotti et al. |
| 6,817,508 | B1 | 11/2004 | Racenet et al. |
| 6,988,650 | B2 | 1/2006 | Schwemberger et al. |
| 7,070,083 | B2 | 7/2006 | Jankowski |
| 7,134,587 | B2 | 11/2006 | Schwemberger et al. |
| 7,147,139 | B2 | 12/2006 | Schwemberger et al. |
| 7,147,140 | B2 | 12/2006 | Wukusick et al. |
| 7,204,404 | B2 | 4/2007 | Nguyen et al. |
| 7,207,472 | B2 | 4/2007 | Wukusick et al. |
| 7,210,609 | B2 | 5/2007 | Leiboff et al. |
| 7,237,708 | B1 | 7/2007 | Guy et al. |
| 7,275,674 | B2 | 10/2007 | Racenet et al. |
| RE40,237 | E | 4/2008 | Bilotti et al. |
| 7,407,076 | B2 | 8/2008 | Racenet et al. |
| 7,431,190 | B2 | 10/2008 | Hoffman |
| 7,522,854 | B2 | 4/2009 | Kinouchi et al. |
| 7,549,563 | B2 | 6/2009 | Mather et al. |
| 7,568,605 | B2 | 8/2009 | Kruszynski |
| 7,641,092 | B2 | 1/2010 | Kruszynski et al. |
| 7,717,312 | B2 | 5/2010 | Beetel |
| 7,731,073 | B2 | 6/2010 | Wixey et al. |
| 7,735,704 | B2 | 6/2010 | Bilotti |
| 7,766,207 | B2 | 8/2010 | Mather et al. |
| 7,810,690 | B2 | 10/2010 | Bilotti et al. |
| 7,886,953 | B2 | 2/2011 | Schwemberger et al. |
| 8,016,176 | B2 | 9/2011 | Kasvikis et al. |
| 8,029,520 | B2 | 10/2011 | Korvick et al. |
| 8,033,439 | B2 | 10/2011 | Racenet et al. |
| 8,070,038 | B2 | 12/2011 | Kostrzewski |
| 8,231,041 | B2 | 7/2012 | Marczyk et al. |
| 8,292,904 | B2 | 10/2012 | Popovic et al. |
| 8,360,296 | B2 | 1/2013 | Zingman |
| 8,371,494 | B2 * | 2/2013 | Racenet .............. A61B 17/072 227/175.1 |
| 8,424,738 | B2 | 4/2013 | Kasvikis |
| 8,499,994 | B2 | 8/2013 | D'Arcangelo |

(56) References Cited

U.S. PATENT DOCUMENTS

| | | |
|---|---|---|
| 8,596,515 B2 | 12/2013 | Okoniewski |
| 8,627,994 B2 | 1/2014 | Zemlok et al. |
| 8,646,673 B2 | 2/2014 | Bilotti et al. |
| 8,757,467 B2 | 6/2014 | Racenet et al. |
| 8,955,732 B2 | 2/2015 | Zemlok et al. |
| 8,967,446 B2 | 3/2015 | Beardsley et al. |
| 9,022,273 B1 | 5/2015 | Marczyk et al. |
| 9,125,651 B2 | 9/2015 | Mandakolathur Vasudevan et al. |
| 9,192,382 B2 | 11/2015 | Kostrzewski |
| 2004/0164123 A1 | 8/2004 | Racenet et al. |
| 2005/0247752 A1 | 11/2005 | Kelly et al. |
| 2005/0247753 A1 | 11/2005 | Kelly et al. |
| 2006/0163312 A1 | 7/2006 | Viola et al. |
| 2007/0039996 A1* | 2/2007 | Mather ............... A61B 17/072 227/176.1 |
| 2007/0095877 A1 | 5/2007 | Racenet et al. |
| 2007/0187456 A1 | 8/2007 | Viola et al. |
| 2009/0302093 A1* | 12/2009 | Kasvikis ............ A61B 17/072 227/180.1 |
| 2010/0048988 A1 | 2/2010 | Pastorelli et al. |
| 2013/0206813 A1 | 8/2013 | Nalagatla |
| 2016/0249914 A1 | 9/2016 | Zhang et al. |
| 2017/0014134 A1 | 1/2017 | Chen et al. |
| 2017/0027571 A1 | 2/2017 | Nalagatla et al. |
| 2017/0027572 A1 | 2/2017 | Nalagatla et al. |
| 2017/0027573 A1 | 2/2017 | Nalagatla et al. |
| 2017/0027574 A1 | 2/2017 | Nalagatla et al. |

FOREIGN PATENT DOCUMENTS

| | | |
|---|---|---|
| CN | 203341778 U | 12/2013 |
| JP | 2012096011 A | 5/2012 |

OTHER PUBLICATIONS

Chinese Office Action dated Sep. 11, 2019 (English translation not available), issued in CN Appln. No. 201480084315.

* cited by examiner

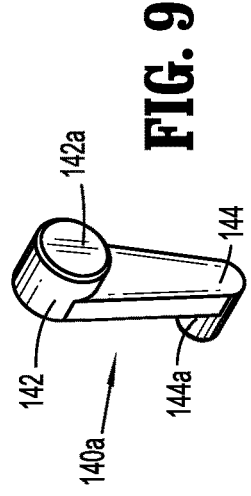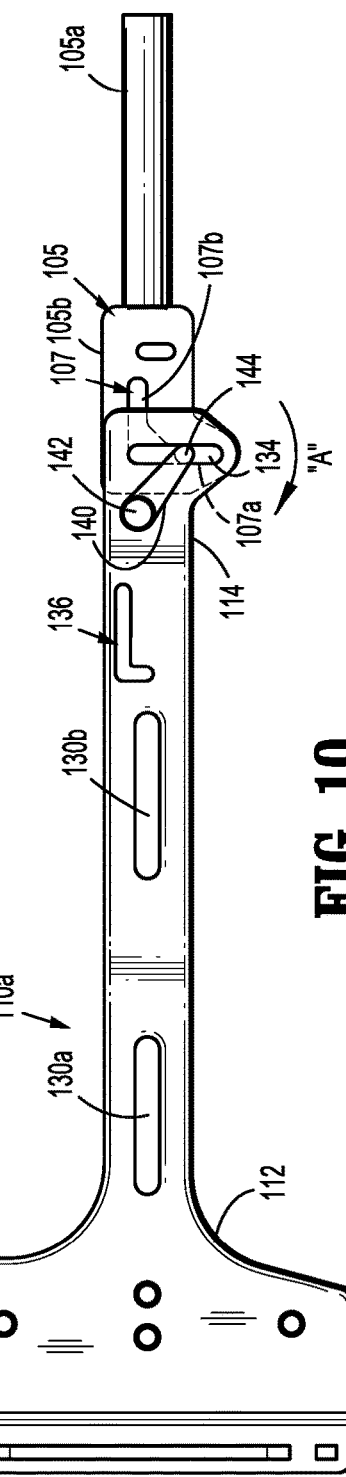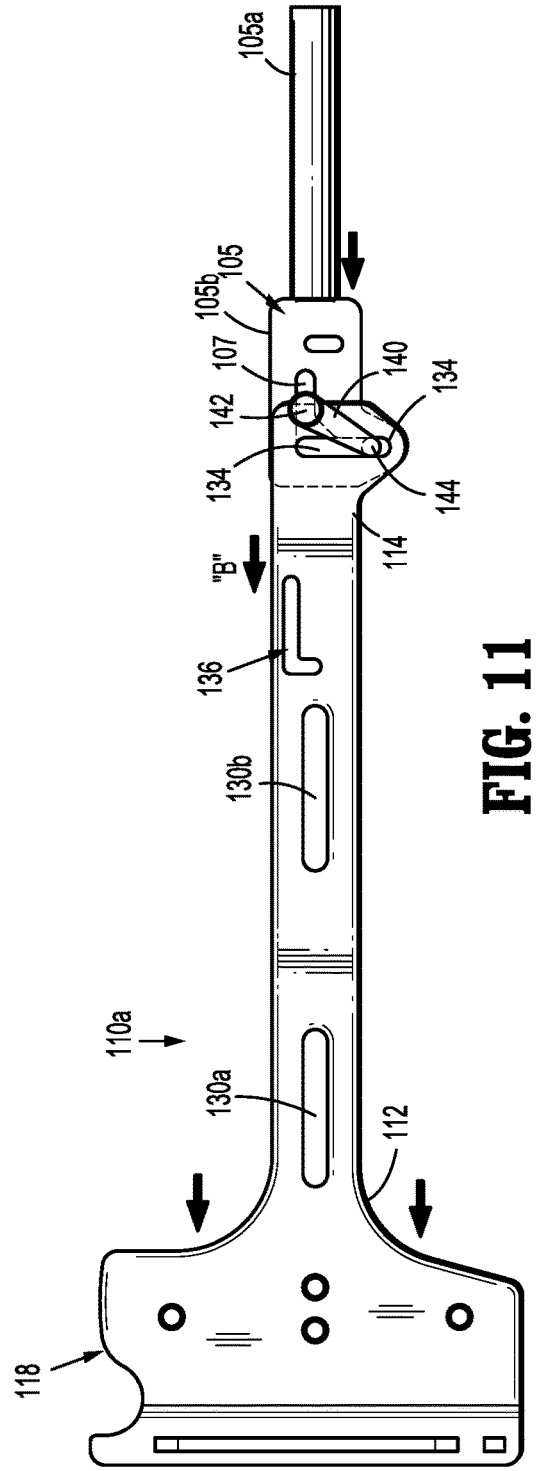

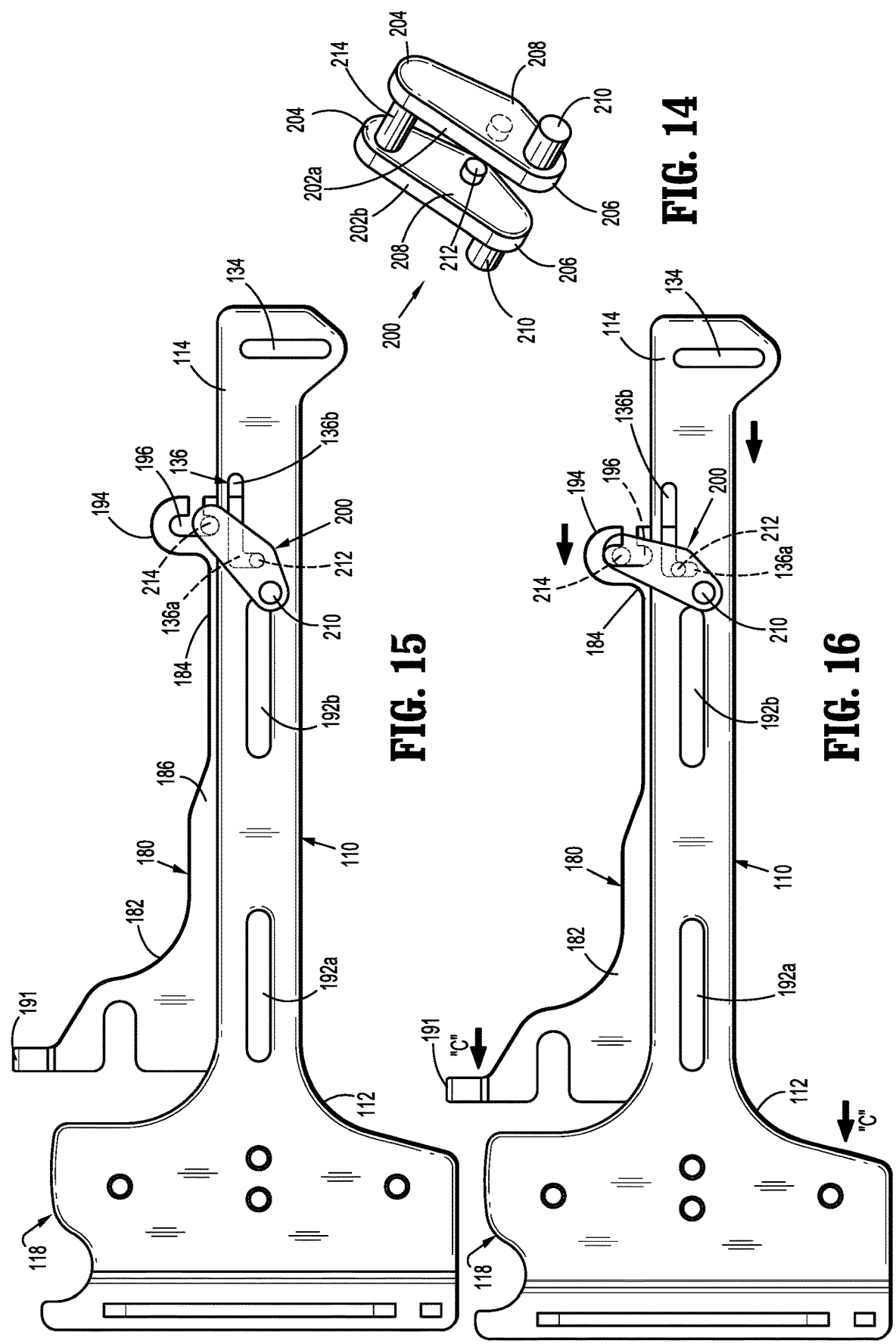

SURGICAL STAPLING DEVICES

CROSS-REFERENCE TO RELATED APPLICATIONS

This application is a National Stage Application of PCT/CN2014/094918 under 35USC § 371 (a), the disclosure of the above-identified application is hereby incorporated by reference in its entirety.

BACKGROUND

1. Technical Field

The present disclosure relates generally to a surgical stapling device and, more specifically, to a surgical stapling device having a single pusher for approximating anvil and cartridge assemblies, for advancing an alignment pin, and for ejecting an array of staples from the cartridge assembly.

2. Background of Related Art

Surgical stapling devices used for applying parallel rows of staples through compressed living tissue are well known in the art, and are commonly used, for example, for closure of tissue or organs prior to transection, prior to resection, or in anastomoses, and for occlusion of organs in thoracic and abdominal procedures.

Typically, such surgical stapling devices include an anvil assembly, a cartridge assembly for supporting an array of surgical staples, an approximation mechanism for approximating the anvil and cartridge assemblies, an alignment pin assembly for capturing tissue between the cartridge and anvil assemblies and for maintaining alignment between the cartridge and anvil assemblies during approximation and firing, and a firing mechanism for ejecting the surgical staples from the cartridge assembly. The approximation mechanism and the firing mechanism generally include distinct actuators for effecting approximation and firing of the staples. The alignment pin assembly can be manually operated to advance an alignment pin from the cartridge assembly into engagement with the anvil or, alternatively, the alignment pin assembly can be automatically actuated upon operation of the approximation mechanism. In instruments having a manually operated alignment pin assembly, the actuator for the alignment pin assembly is disposed at a location spaced from the handle of the instrument.

U.S. Pat. No. 4,930,503 to Pruitt discloses such a surgical stapling device. Pruitt's instrument includes a manually operated alignment pin assembly, an approximation mechanism including a rotatable knob actuator and a firing mechanism including a pivotable trigger. In use, a surgeon must first approximate the anvil and cartridge members by rotating the knob actuator.

Next, the surgeon can advance the alignment pin assembly by advancing a knob supported on the central body portion of the instrument. Thereafter, the instrument can be fired by pivoting the trigger towards a stationary handle of the instrument.

U.S. Pat. No. 5,697,543 to Burdorff also discloses a surgical stapling device having an approximation mechanism, a firing mechanism and an alignment pin mechanism. The approximation and firing mechanisms each include a distinct pivotable trigger actuator. The alignment pin mechanism is operatively associated with the approximation mechanism such that upon actuation of the approximation mechanism, the alignment pin assembly is automatically advanced.

Known prior art surgical staplers are lacking in several respects. Firstly, the use of multiple actuators to effect approximation and firing of the instruments complicate the manufacture and operation of the instrument and, in most cases, require the surgeon to use two hands to hold and operate the instrument. Secondly, the instruments in which the alignment pin assembly is operatively associated with the approximation mechanism require that the instrument be approximated to advance the alignment pin assembly, despite the fact that a surgeon may prefer to advance the alignment pin assembly prior to approximation. In contrast, the instruments in which the alignment pin assembly is manually advanced typically require the surgeon to use a second hand to actuate the alignment pin assembly.

Accordingly, a continuing need exists for a surgical stapling device that can be operated by a surgeon with a single hand and which includes an alignment pin assembly, which can be automatically or manually advanced.

SUMMARY

In one aspect of the present disclosure, a surgical stapling device is provided. The surgical stapling device includes a frame, an anvil, a pusher, a clamping plate assembly, a cartridge, a holder, and a stapling plate. The frame has a proximal end and a distal end. The anvil is supported on the distal end of the frame, and the pusher is supported on the proximal end of the frame. The pusher is movable in relation to the frame between a retracted position and an advanced position. The clamping plate assembly is supported by the frame and has a proximal end and a distal end. The clamping plate assembly is movable in relation to the frame between retracted and advanced positions. The cartridge is supported on the distal end of the clamping plate assembly and is movable in relation to the anvil between an unapproximated position and an approximated position in response to movement of the clamping plate assembly between its retracted and advanced positions. The cartridge includes an alignment pin, which is movable between a retracted position and an advanced position. The holder is supported on the frame and is movable to effect movement of the alignment pin between its retracted and advanced positions. The stapling plate is supported by the frame and is movable between retracted and advanced positions. The pusher is operatively associated with the holder, the clamping plate assembly, and the stapling plate such that movement of the pusher between its retracted and advanced positions effects movement of the holder, the clamping plate assembly, and the stapling plate between their respective retracted and advanced positions.

In some embodiments, the surgical stapling device may include a first pivoting member that includes a first end and a second end. The first end may be pivotably coupled to the frame, and the second end may be operatively coupled to the pusher and the clamping plate assembly such that longitudinal movement of the pusher effects rotation of the first pivoting member to effect longitudinal movement of the clamping plate assembly. The proximal end of the clamping plate assembly may define a vertical slot, and the second end of the first pivoting member may ride along the vertical slot of the clamping plate assembly as the first pivoting member rotates relative to the frame. The pusher may define a slot having a vertical portion and a horizontal portion. The second end of the first pivoting member may be movable from the vertical portion, in which the first pivoting member is rotatable relative to the frame in response to movement of the pusher, to the horizontal portion, in which the first pivoting member is not rotatable relative to the frame in response to movement of the pusher.

It is contemplated that the surgical stapling device may further include a second pivoting member that includes a first end, a second end, and an intermediate portion. The first end may be operatively coupled to the holder, and the second end may be pivotably coupled to the frame. The intermediate portion may be operatively coupled to the clamping plate assembly such that longitudinal movement of the clamping plate assembly via longitudinal movement of the pusher rotates the second pivoting member to effect longitudinal movement of the holder relative to the clamping plate assembly. The clamping plate assembly may define a slot having a vertical portion and a horizontal portion. The intermediate portion of the second pivoting member may be movable from a position in the vertical portion of the slot of the clamping plate assembly, in which the second pivoting member is rotatable relative to the frame in response to movement of the clamping plate assembly, to a position in the horizontal portion of the slot of the clamping plate assembly, in which the second pivoting member does not rotate relative to the frame in response to movement of the clamping plate assembly. The second end of the second pivoting member may be radially offset from the intermediate portion of the second pivoting member.

It is envisioned that the holder may define a vertical slot, and the second end of the second pivoting member may ride along the vertical slot of the holder as the second pivoting member rotates relative to the frame.

In some embodiments, the stapling plate may be operatively associated with the pusher such that longitudinal movement of the pusher results in corresponding longitudinal movement of the stapling plate.

It is contemplated that the surgical stapling device may include a staple pushing member movably disposed adjacent the cartridge, and the stapling plate may be in abutment with the staple pushing member such that the staple pushing member moves longitudinally in response to longitudinal movement of the stapling plate.

It is envisioned that the surgical stapling device may further include a handle assembly configured to be coupled to the proximal end of the frame. A loading unit may be provided that includes the frame, the pusher, the clamping plate assembly, the anvil, the cartridge, the holder, and the stapling plate. The loading unit is configured to be releasably coupled to the handle assembly.

In another aspect of the present disclosure, a surgical stapling device is provided that includes a frame, a pusher, a clamping plate assembly, a holder, and a stapling plate. The frame has a proximal end and a distal end. The pusher is supported on the proximal end of the frame and is movable in relation to the frame between a retracted position and an advanced position. The clamping plate assembly is supported by the frame and has a proximal end and a distal end. The clamping plate assembly is movable in relation to the frame between retracted and advanced positions to effect movement of a cartridge between a retracted position and an advanced position. The holder is supported on the frame and is movable to effect movement of an alignment pin between a retracted position and an advanced position. The stapling plate is supported by the frame and is movable between retracted and advanced positions. The pusher is operatively associated with the holder, the clamping plate assembly, and the stapling plate such that movement of the pusher between its retracted and advanced positions effects movement of the holder, the clamping plate assembly, and the stapling plate between their respective retracted and advanced positions.

It is envisioned that the surgical stapling device may further include a handle assembly configured to be coupled to the proximal end of the frame. A loading unit may be provided that includes the frame, the pusher, the clamping plate assembly, the holder, and the stapling plate. The loading unit is configured to be releasably coupled to the handle assembly.

BRIEF DESCRIPTION OF THE DRAWINGS

Embodiments of the presently disclosed surgical stapling apparatus are described herein with reference to the drawings, wherein:

FIG. 9 is an enlarged view of the indicated area of detail shown in FIG. 5 illustrating a first pivoting member;

FIG. 10 is a side view of the loading unit of FIG. 3 with parts removed to illustrate a clamping plate assembly in a retracted position;

FIG. 11 is a side view of the loading unit of FIG. 3 with parts removed to illustrate the clamping plate assembly in a partially advanced position;

FIG. 14 is an enlarged view of the indicated area of detail shown in FIG. 5 illustrating a second pivoting member;

FIG. 15 is a side view of the loading unit of FIG. 3 with parts removed to illustrate a holder in a retracted position relative to the clamping plate assembly;

FIG. 16 is a side view of the loading unit of FIG. 3 with parts removed to illustrate the holder in a partially advanced position relative to the clamping plate assembly;

DETAILED DESCRIPTION

Figure 1:
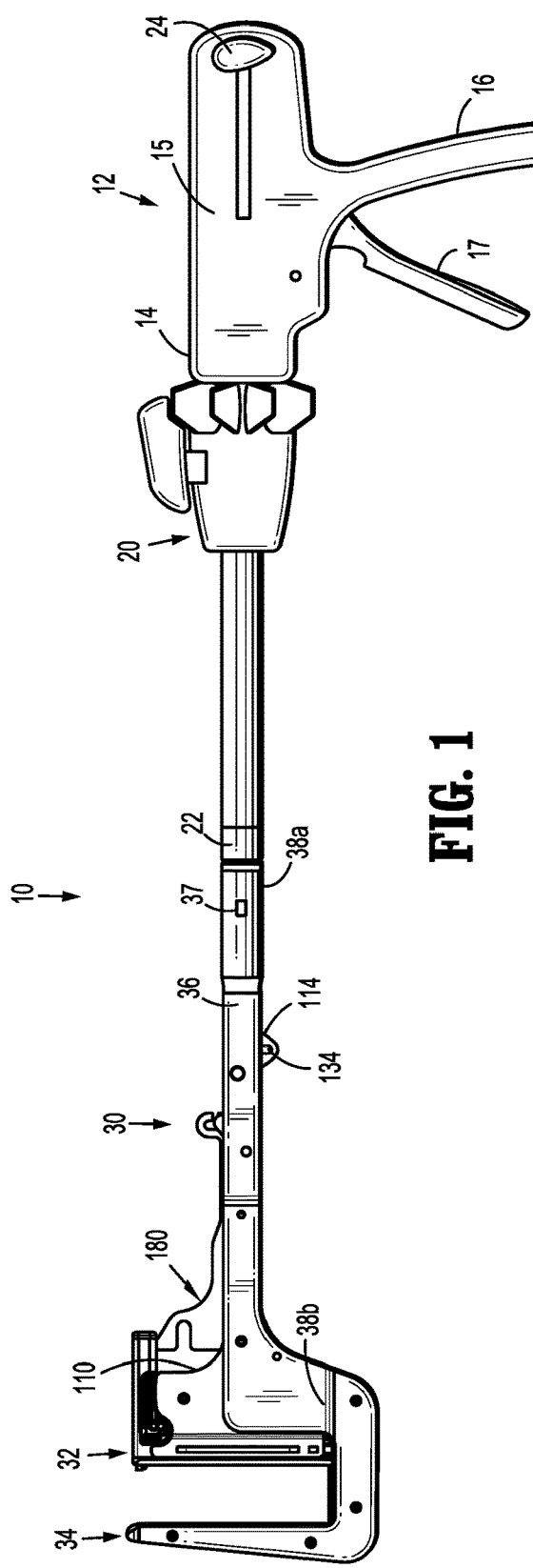
FIG. 1 is a side view of one embodiment of the presently disclosed surgical stapling device including a loading unit.

Embodiments of the presently disclosed surgical stapling device will now be described in detail with reference to the drawings, wherein like reference numerals designate corresponding elements in each of the several views.

As used herein, the term distal refers to that portion of the instrument, which is farthest from a clinician, while the term proximal refers to that portion of the instrument, which is closest to the clinician. In addition, as used herein, the term clinician refers to medical staff including doctors, nurses and support personnel.

Figure 2:
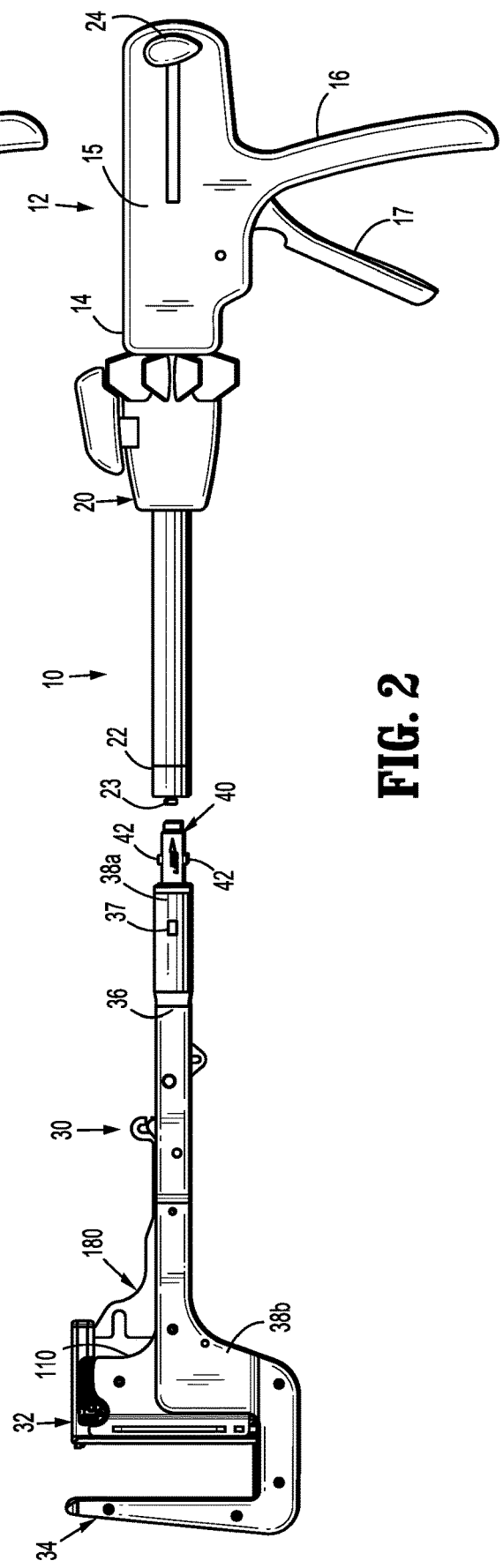
FIG. 2 is a side view of the surgical stapling device shown in FIG. 1 illustrating the loading unit de-coupled from the handle assembly.

With reference to FIGS. 1 and 2, the presently disclosed surgical stapling device is designated generally by reference numeral 10. Surgical stapling device 10 includes a handle assembly 12, an adapter assembly 20 coupled to a distal end 14 of the handle assembly 12, and a surgical loading unit 30 coupled to a distal end 22 of the adapter assembly 20. The handle assembly 12 includes a body 15 having a stationary handle 16 and a pivotable trigger 17. The trigger 17 is operatively coupled to a drive shaft 23 such that actuation of the trigger 17 longitudinally translates the drive shaft 23. When the loading unit 30 is coupled to the adapter assembly 20, the drive shaft 23 engages the loading unit 30 such that longitudinal translation of the drive shaft 23 effects operation of three different mechanisms of the loading unit 30, as will be discussed in detail below. A manual engagement member or thumb button 24 is slidably positioned on each side of the body 15. The thumb buttons 24 are operatively associated with the drive shaft 23 and can be pulled proximally by a clinician to retract the drive shaft 23 within the adapter assembly 20.

With reference to FIGS. 1-5, the loading unit 30 is configured to clamp and staple tissue disposed between the cartridge assembly 32 and the anvil assembly 34. The loading unit 30 is selectively connectable to the distal end 22 of the adapter assembly 20. In some embodiments, the loading unit 30 may be selectively connectable directly to an electromechanical handle assembly, a surgical robotic system, or any other suitable actuation mechanism. The loading unit 30 includes a frame 36 having a proximal end 38a and a distal end 38b. The frame 36 is removably coupled to the adapter assembly 20 via a coupling member 40. The coupling member 40 has a proximal end 40a and a distal end 40b. The proximal end 40a is configured to be removably coupled to the distal end 22 of the adapter assembly 20 via a mating engagement between bosses 42 of the coupling member 40 and an engagement structure (not shown) formed on the distal end 22 of the adapter assembly 20. The distal end 40b of the coupling member 40 includes a pair of bosses 43, which are received within correspondingly shaped holes 37 formed in the proximal end 38a of the frame 36 to secure the coupling member 40 to the frame 36.

The frame 36 has a first side 44a and a second side 44b spaced from first side 44a. The first and second sides 44a, 44b, respectively, of the frame 36 define a longitudinal channel 46 (FIG. 3) that receives various moving components of the loading unit 30, as will be described in detail below. The distal end 38b of the frame 36 has a hooked configuration and extends perpendicularly relative to a longitudinal axis X (FIG. 3) of the frame 36. The distal end 38b of the frame 36 supports the anvil assembly 34 and guides movement of the cartridge assembly 32 in relation to the anvil assembly 34 to orient the anvil assembly 34 in a side-by-side orientation with the cartridge assembly 32 when the cartridge assembly is in an advanced position.

An intermediary portion 45 of the frame 36 defines a first opening or pivot hole 48 in each side frame 44a, 44b that receives a first pivoting member 140. The intermediary portion 45 also defines a second opening or pivot hole 50 in each side frame 44a, 44b that receives a second pivoting member 200, as will be described in greater detail below.

Figure 3:
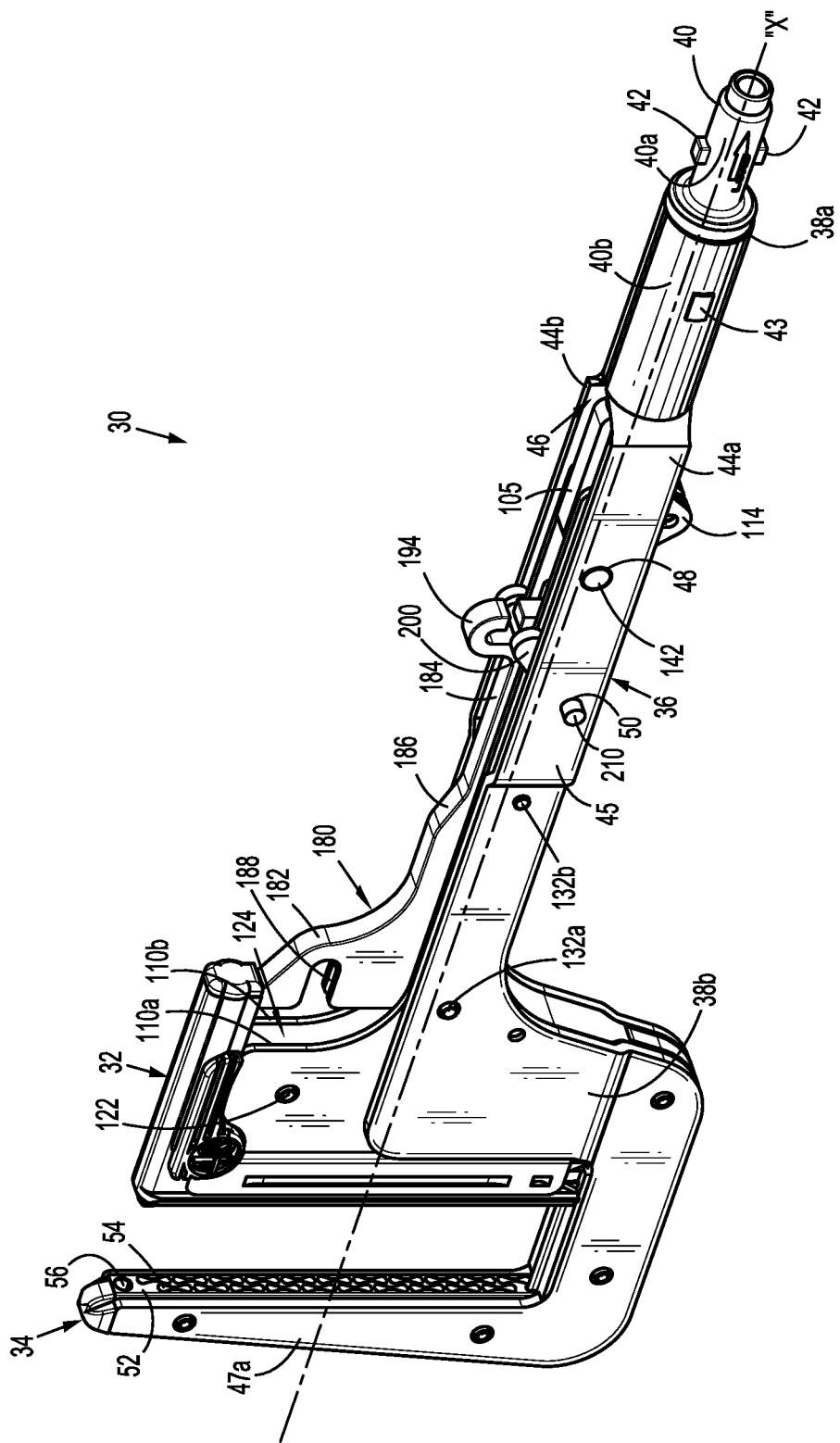
FIG. 3 is a perspective view of the loading unit shown in FIG. 1.
Figure 4:
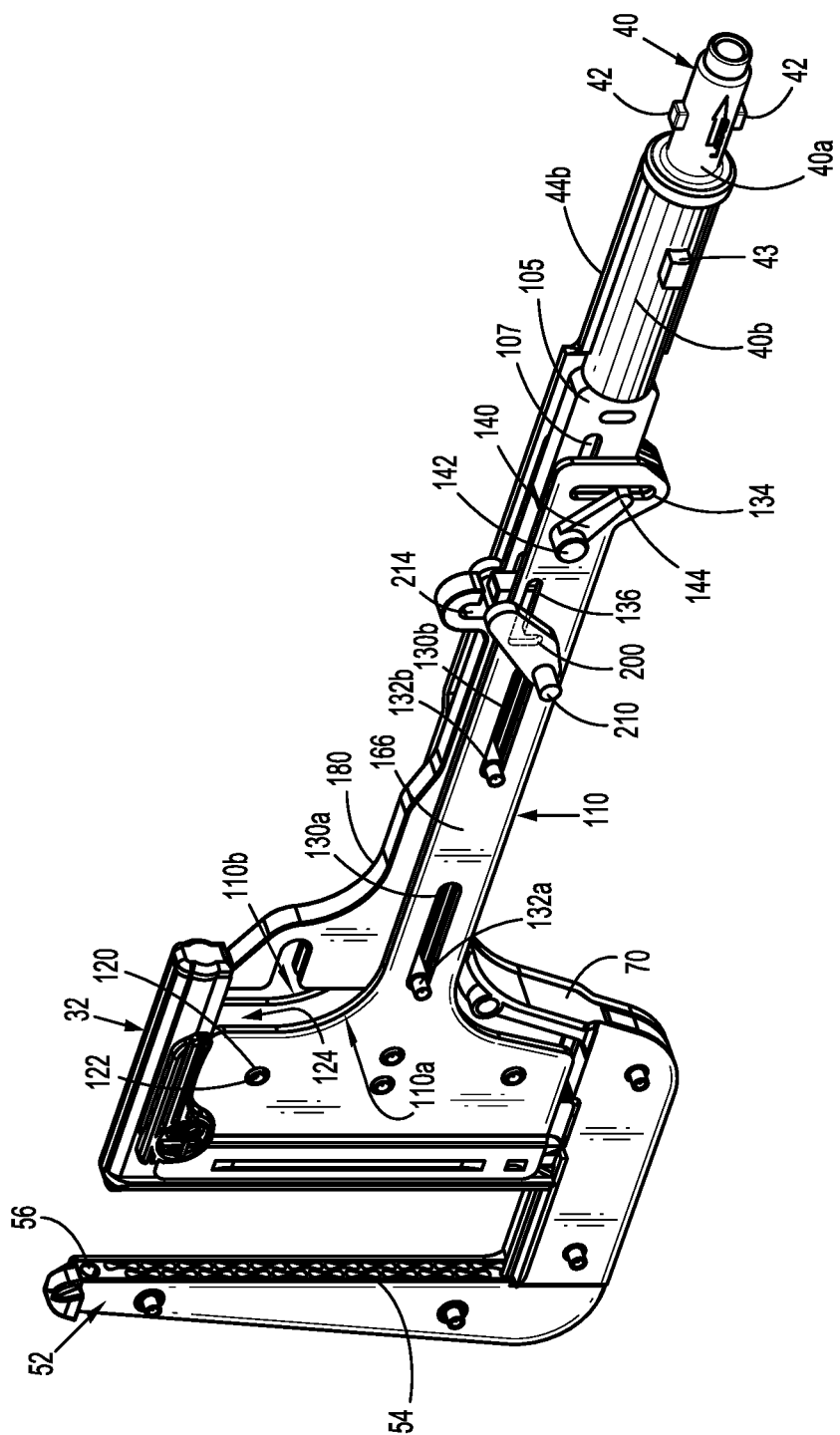
FIG. 4 is a perspective view of the loading unit shown in FIG. 3 with a portion of a frame of the loading unit cutaway.
Figure 5:
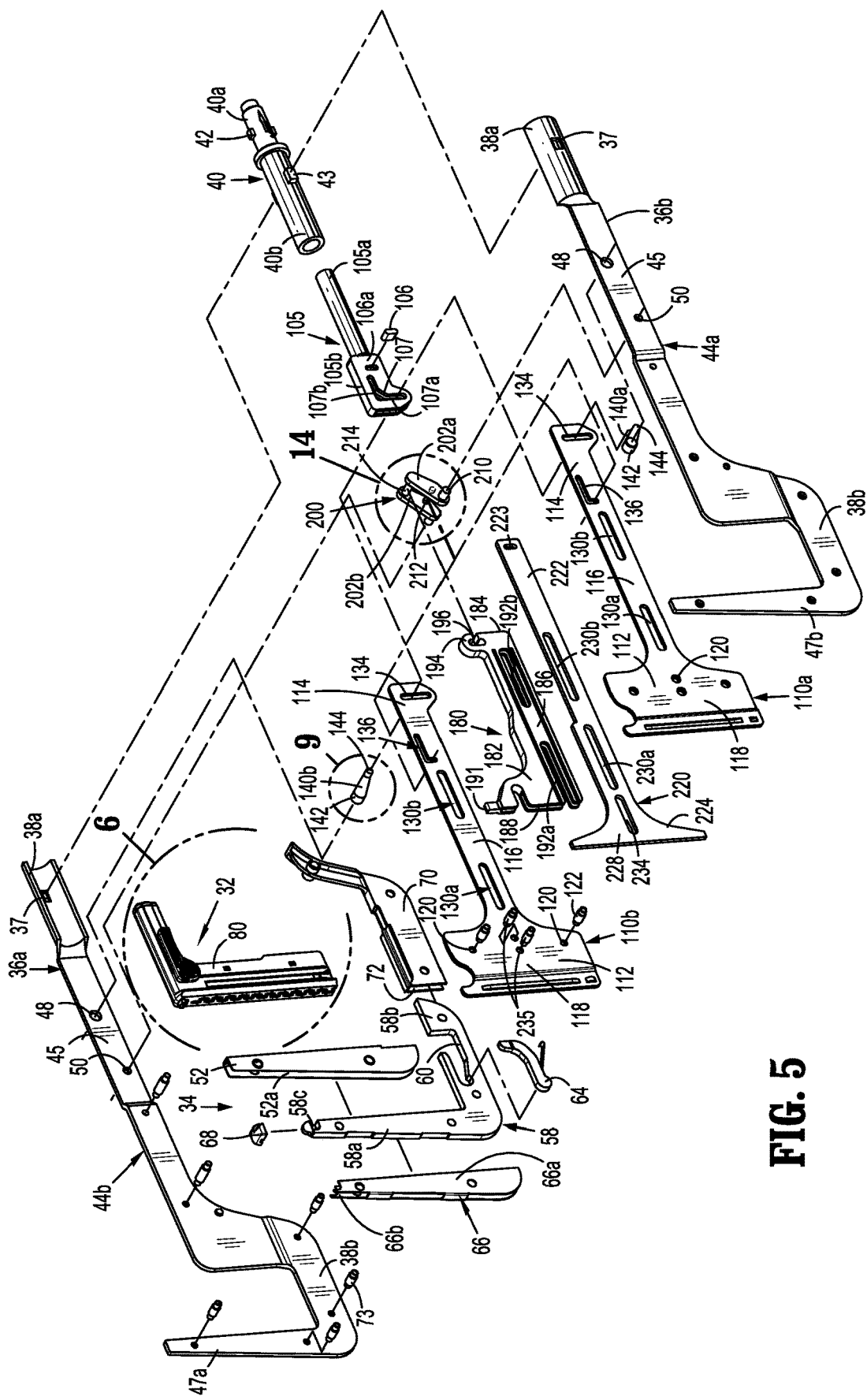
FIG. 5 is a perspective view with parts separated of the loading unit shown in FIG. 3.
Figure 6:
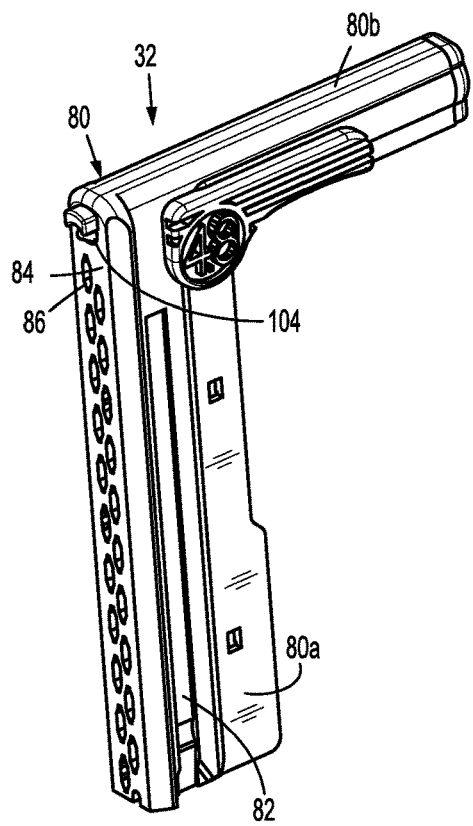
FIG. 6 is an enlarged view of the indicated area of detail shown in FIG. 5 illustrating a cartridge assembly of the loading unit.

Referring to FIGS. 3-5, the anvil assembly 34 includes an anvil 52 supported on the distal end 38b of the frame 36. The anvil 52 defines a plurality of staple pockets 54 formed in the surface of the anvil 52 which are configured to form staples ejected from the cartridge assembly 32. The anvil 52 defines a bore 56 configured for passage of an alignment pin 96, as will be described in further detail below.

The anvil assembly 34 further includes a stiffener plate 58, a spacer plate 66, and a t-track 70. The stiffener plate 58 has a vertical portion 58a and a horizontal portion 58b. The vertical portion 58a of the stiffener plate 58 is disposed within a channel 52a of the anvil 52 and defines a notch 58c. The notch 58c is in alignment with the bore 56 of the anvil 52 and is configured to receive a distal end 96a of the alignment pin 96 as will be discussed in further detail below. The horizontal portion 58b of the stiffener plate 58 defines a cutout 60 that is dimensioned to receive an interlock member 64. In the assembled state, the vertical portion 58a of the stiffener plate 58 is positioned between a vertical portion 47a, 48b of each respective frame side 44a, 44b.

The spacer plate 66 includes a pair of legs 66a, 66b (FIG. 5) positioned on opposite sides of the stiffener plate 58 within the channel 52a of the anvil 52 between the stiffener plate 58 and the anvil 52. The anvil assembly 34 includes a cap 68 that is positioned over an upper end of the anvil 52, stiffener plate 58 and spacer plate 66 to provide a smooth surface that is less likely to snag tissue during use.

The t-track 70 of the anvil assembly 34 defines a channel 72 that receives the horizontal portion 58b of the stiffener plate 58. The t-track 70 is positioned about the cutout 60 in the horizontal portion 58b to define a cavity in which the interlock 64 is positioned.

The components of the anvil assembly 34 are secured to the frame sides 44a, 44b using rivets 73. Alternately, other fastening members may be used to secure the components of the anvil assembly 34 to the frame sides 44a, 44b including screws, pins, welding, etc. In embodiments, the components of the anvil assembly 34 are formed of stainless steel. Alternately, other materials, including metals, having requisite strength requirements can be used to form some or all of the components of the anvil assembly 34.

Referring to FIGS. 5-8, the cartridge assembly 32 is movable along an axis parallel to the longitudinal axis of the loading unit 30 from a position spaced from the anvil assembly 34 to a position in close approximation with the anvil assembly 34 to clamp and staple tissue. The cartridge assembly 32 includes a cartridge 80, a pusher assembly 90, a plurality of staples 91, and an alignment pin 96. The cartridge 80 has a first or vertical portion 80a and a second or horizontal portion 80b extending perpendicularly from the first portion 80a. The first portion 80a has an elongate slot 82 defined in each opposing side of the cartridge 80. Each elongate slot 82 is configured to receive elongate projections 128 formed on a respective clamping plate 116 of the clamping plate assembly 110 (FIG. 8) to frictionally secure the cartridge assembly 32 to the clamping plate assembly 110. The first portion 80a of cartridge 80 has a distally-oriented, tissue engaging surface 84 that defines an array of staple receiving slots 86 and a proximally facing cavity 88 that communicates with the staple receiving slots 86.

The staple pusher assembly 90 includes a plurality of independently movable staple pushing members 90a, 90b movably disposed within the cavity 88 of the first portion 80a. Each pushing member 90a, 90b includes a plurality of fingers 92, which are slidably received within respective staple receiving slots 86. The fingers 92 are positioned proximally of the staples 91 within the slots 86, such that advancement of the fingers 92 within the slots 86 effects ejection of the staples 91 from the slots 86. As illustrated, the staple pusher assembly 90 includes two pusher members 90a, 90b that form the pusher assembly 90. In some embodiments, the pusher assembly 90 may be modified to include one or more pusher members. For example, the cartridge assembly 32 can include a single pusher member or three independently movable pusher members.

Figure 7:
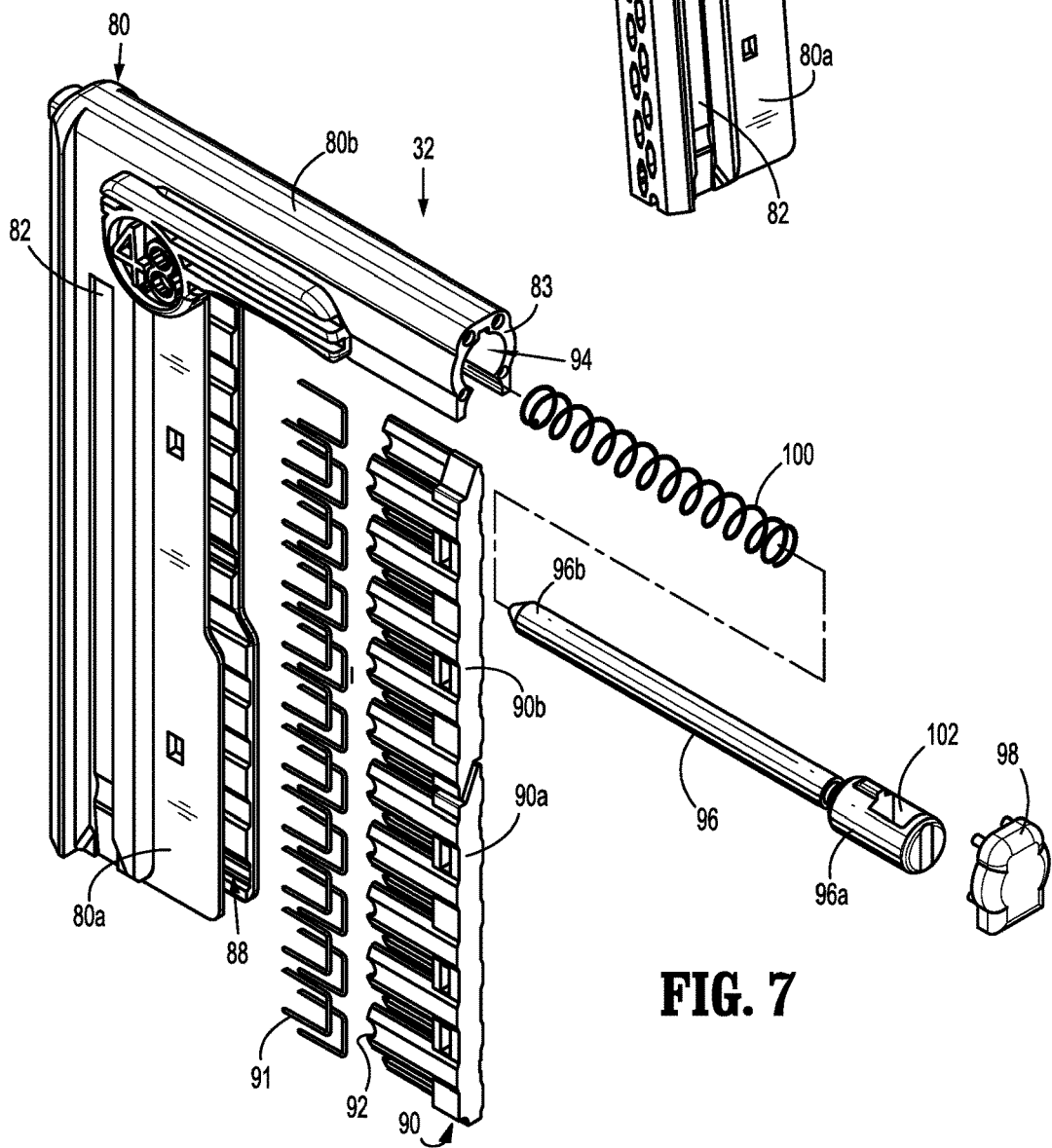
FIG. 7 is a perspective view, with parts separated, of a cartridge assembly including a cartridge, an alignment pin, a staple pusher assembly, and a plurality of staples.

The second or horizontal portion 80b of the cartridge 80 extends parallel to a longitudinal axis "X" defined by the frame 36 (FIG. 3) and defines a guide channel 94 (FIG. 7). The second portion 80b supports the alignment pin 96, a channel cover 98, and a spring 100. The alignment pin 96 is slidably supported in the guide channel 94 and has a proximal end 96a and a distal end 96b. The channel cover 98 is connected to a proximal end 83 of the second portion 80b of the cartridge 80 to close the guide channel 94. The spring 100 is disposed within the guide channel 94 between a distal end of the horizontal portion 80b of the cartridge 80 and the proximal end 96a of the alignment pin 96 to resiliently bias the alignment pin 96 to a retracted position within the guide channel 94. The proximal end 96a of the alignment pin 96 defines an orifice 102. The orifice 102 is configured to receive an abutment member 191 of an alignment pin holder 180 (FIG. 23) such that advancement of the holder 180 effects advancement of the alignment pin 96, as described in detail below.

The distally-oriented face 84 of the cartridge 80 defines a bore 104 (FIG. 6) that is coaxial and in communication with the guide channel 94. The bore 104 is dimensioned to receive the distal end 96b of the alignment pin 96 to allow the alignment pin 96 to extend from within the guide channel 94 of the cartridge 80, through the anvil bore 56 (FIGS. 24 and 25), and into the notch 58c formed in the stiffener plate 58 of the anvil assembly 34, as will be discussed in further detail below.

With reference again to FIGS. 3-5, the loading unit 30 of the surgical stapling device 10 includes three mechanisms including the clamping plate assembly 110, the alignment pin holder 180, and a stapling plate 220. The clamping plate assembly 110 operates to approximate the cartridge assembly 32 and the anvil assembly 34; the holder 180 operates to move the alignment pin 96 between retracted and advanced positions; and the stapling plate 220 operates to move the staple pushing members 90a, 90b to eject staples 91 from the cartridge 80 into tissue. The clamping plate assembly 110, the alignment pin holder 180, and the stapling plate 220 are movably supported between frame sides 44a and 44b of the frame 36 between retracted and advanced positions in response to movement of a pusher 105. The pusher 105 is operatively coupled to the drive shaft 23 of the stapling device 10 when the loading unit 30 is coupled to the stapling device 10 such that movement of the trigger 17 of the handle assembly 12 of the stapling device 10 effects movement of the pusher 105 and, thus, effects operation of the clamping plate assembly 110, the holder 180, and the stapling plate 220, as will be discussed in further detail below.

The pusher 105 is slidably supported within the coupling member 40 of the loading unit 100 between retracted and advanced positions. The pusher 105 has a proximal end 105a and a distal end 105b. The proximal end 105a of the pusher 105 is configured to receive and operatively engage a distal end of the drive shaft 23 of the stapling device 10 (FIG. 2) such that longitudinal movement of the drive shaft 23, in response to actuation of the trigger 17 of the handle assembly 12, results in a corresponding longitudinal motion of the pusher 105. The distal end 105b of the pusher 105 is operatively associated with the clamping plate assembly 110, the alignment pin holder 180, and the stapling plate 220 such that advancement of the pusher 105 actuates the clamping plate assembly 110, the alignment pin holder 180, and the stapling plate 220 as discussed below.

The distal end 105b of the pusher 105 defines a bore 106a (FIG. 5) that receives a pin 106. The pin 106 extends through the bore 106a and is received within a hole 223 defined in the stapling plate 220 to fixedly connect the pusher 105 with the stapling plate 220. As such, advancement of the pusher 105 causes corresponding advancement of the stapling plate 220.

The distal end 105b of the pusher 105 also defines a slot 107. A pivoting member 140 is provided to couple the pusher 105 to the clamping plate assembly 110. The pivoting member 140 has a first end 144 adapted to be coupled to the pusher 105 and a second end adapted to be coupled to the clamping plate assembly 110 such that advancement of the pusher 105 also effects advancement of the clamping plate assembly 110, as described in detail below.

With reference to FIGS. 5-8, the clamping plate assembly 110 includes clamp slide members 110a, 110b. Each clamp slide member 110a, 110b has a distal end 112, a proximal end 114, and an elongated body 116 extending therebetween. The distal end 112 of each clamp slide member 110a, 110b includes a head portion 118. Each head portion 118 has a plurality of openings 120 configured to receive a fastening member 122 for securing clamp slide members 110a, 110b together in spaced relation to each other. In the assembled state, clamp slide members 110a, 110b are spaced from each other to define an elongated channel 124, which slidably receives the alignment pin holder 180 and the stapling plate 220 and releasably supports the cartridge assembly 32.

Figure 8:
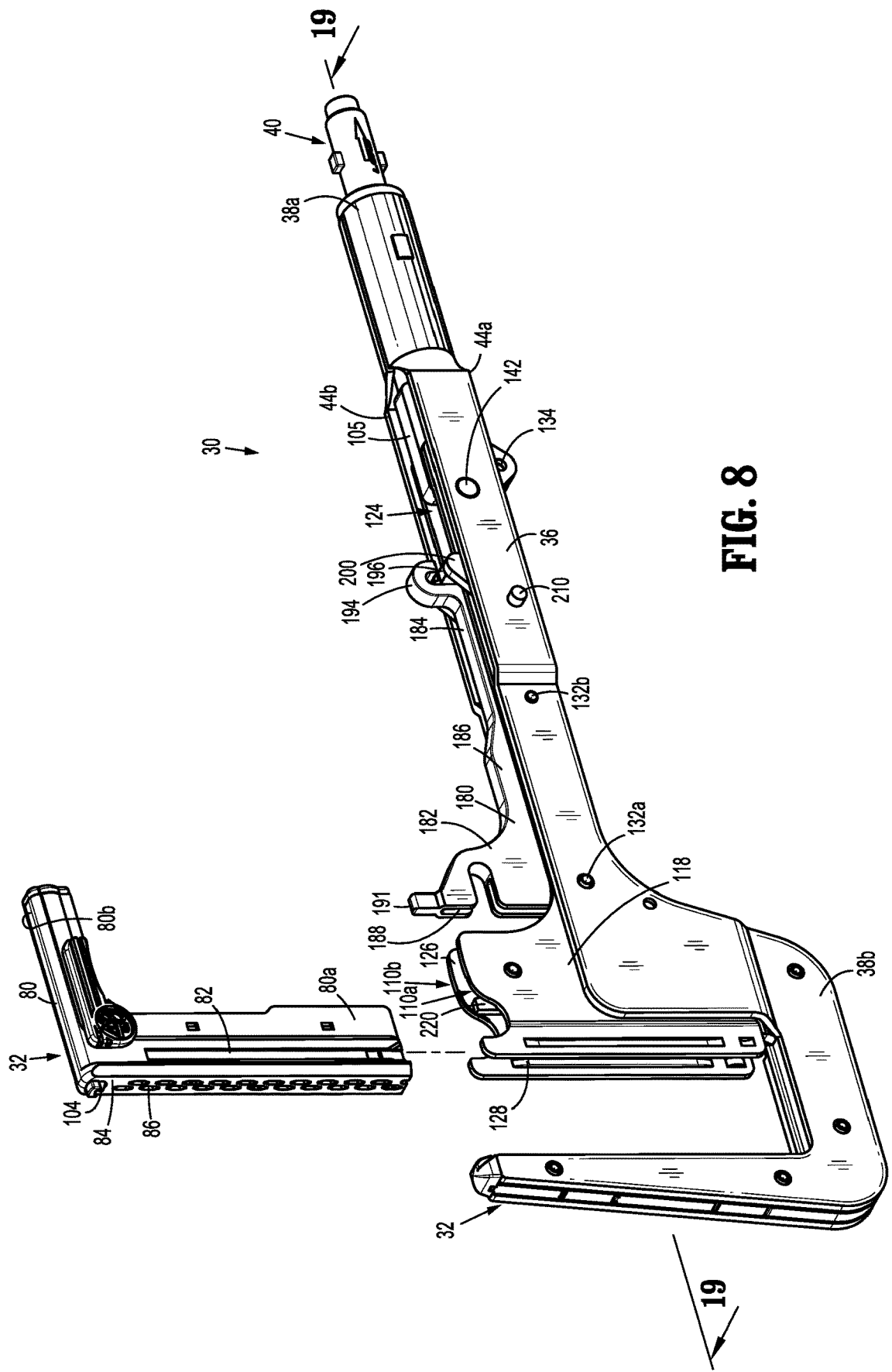
FIG. 8 is a perspective view of the loading unit of FIG. 3 with the cartridge assembly of FIG. 6 separated.

With reference to FIG. 8, the head portions 118 of the clamp slide members 110a, 110b define a cartridge support receptacle 126 that is configured to releasably support the cartridge assembly 32. As discussed above, each clamp slide member 110a, 110b includes an elongate projection 128 that extends into the cartridge support receptacle 126. Upon placement of the cartridge assembly 32 within the receptacle 126 of the clamping plate assembly 110, each of the elongate slots 82 of the cartridge 80 receive a respective elongate projection 128 of a clamp slide member 110a, 110b to retain the cartridge assembly 32 within the cartridge support receptacle 126. As such, when the cartridge assembly 32 is placed within the cartridge support receptacle 126 of the clamping plate assembly 110 and the clamping plate assembly 110 is moved between retracted and advanced positions, the entire cartridge assembly 32 moves with the clamping plate assembly 110 in relation to the anvil assembly 34 between spaced and approximated positions.

The elongated body 116 of each clamp slide member 110a, 110b includes a pair of elongated guide slots 130a, 130b (FIG. 5). The guide slots 130a, 130b slidably receive pins 132a, 132b, respectively, which extend between and interconnect the frame sides 44a, 44b. The pins 132a, 132b are positioned in the guide slots 130a, 130b to maintain alignment of the clamp slide members 110a, 110b between the frame sides 44a, 44b during movement of the clamp slide members 110a, 110b between the advanced and retracted positions and to limit the extent of longitudinal movement of the clamp slide members 110a, 110b. More specifically, engagement of the pins 132a, 132b with the proximal ends of the guide slots 130a, 130b, respectively, prevents further distal movement clamping plate assembly 110 in relation to the frame 36 and defines the fully advanced position of the clamping plate assembly 110. In addition, engagement of the pins 132a, 132b with the distal ends of the guide slots 130a, 130b, respectively, prevents further proximal movement of the clamping plate assembly 110 in relation to the frame 36 and defines the fully retracted position of the clamping assembly 110.

With reference also to FIGS. 9-13, the proximal end 114 of each clamp slide member 110a, 110b defines first and second slots 134 and 136, respectively. In embodiments, the first slot 134 is a vertical slot and the second slot 136 is an L-shaped slot. The vertical slot 134 is disposed proximally of the L-shaped slot 136 and is in alignment with a portion of the slot 107 of the pusher 105. The pivoting member 140 includes a first rocker or cam member 140a which interconnects the frame side 44a to the clamp slide member 110a. The pivoting member 140 can also include a second rocker or cam member 140b to interconnect the frame side 44b to the clamp slide member 110b. Each cam member 140a, 140b has a first end 142 and a second end 144. The first end 142 of the first cam member 140a includes a protrusion 142a that is pivotably received within the pivot hole 48 defined in the left frame side 44a and the first end 142 of the second cam member 140b is pivotably received within the pivot hole 50 defined within the right frame side 44b. The second end 144 of each cam member 140a, 140b defines a protrusion 144a that extends through the vertical slots 134 of a respective clamp slide member 110a, 110b and the slot 107 of the pusher 105 to operatively couple the clamping plate assembly 110 with the pusher 105. As such, when the pusher 105 is advanced, the cam members 140a and 140b are pivoted about the protrusion 142a formed at the first ends 142 of the cam members 140a and 140b. As the cam members 140a and 140b are pivoted in response to movement of the pusher 105, engagement of protrusion 144a with clamp slide members 110a, 110b causes movement of the clamp slide members 110a, 110b, as will be discussed in detail below.

With continued reference to FIGS. 10-13, the slot 107 of the pusher 105 has a vertical portion 107a and a horizontal portion 107b that communicate with one another. In a retracted position of the pusher 105, the protrusion 144b at the second end 144 of each cam member 140a, 140b is slidably captured within the respective vertical slots 134 of the clamp slide members 110a, 110b of the clamping plate assembly 110 and the vertical portion 107a of the slot 107 of the pusher 105. As such, as the pusher 105 is advanced distally, walls defining the vertical portion 107a of the slot 107 of the pusher 105 engage the protrusion 144a formed at the second end 144 of each cam member 140a, 140b to rotate the cam members 140a, 140b relative to the frame 36, in a direction indicated by arrow "A" in FIG. 10, toward a semi-advanced position, as shown in FIG. 11. Rotation of the cam members 140a, 140b urges the clamping plate assembly 110 in a distal direction relative to the frame 36, as indicated by arrow "B" in FIG. 11. The vertical slots 134 of the clamping plate assembly 110 also allow the protrusion 144a formed at the second end 144 of each cam member 140a, 140b to ride from a bottom end of each respective vertical slot 134 towards a top end of each of the vertical slots 134 as the cam members 140a, 140b rotate.

Figure 12:
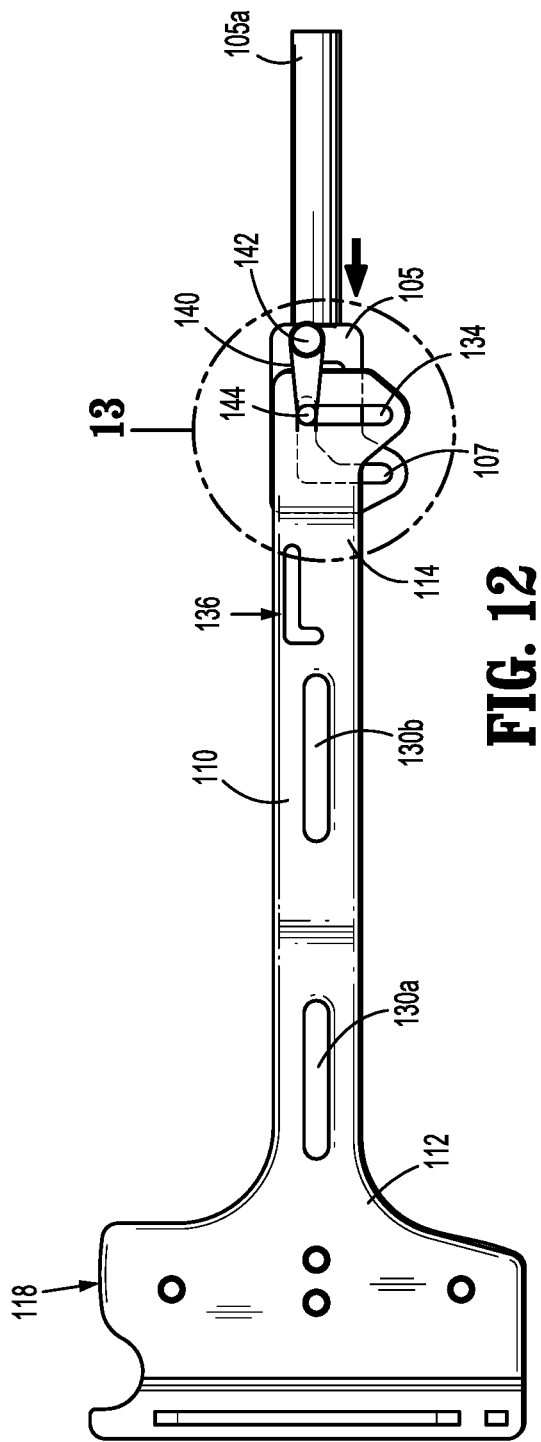
FIG. 12 is a side view of the loading unit of FIG. 3 with parts removed to illustrate the clamping plate assembly in a fully advanced position.
Figure 13:
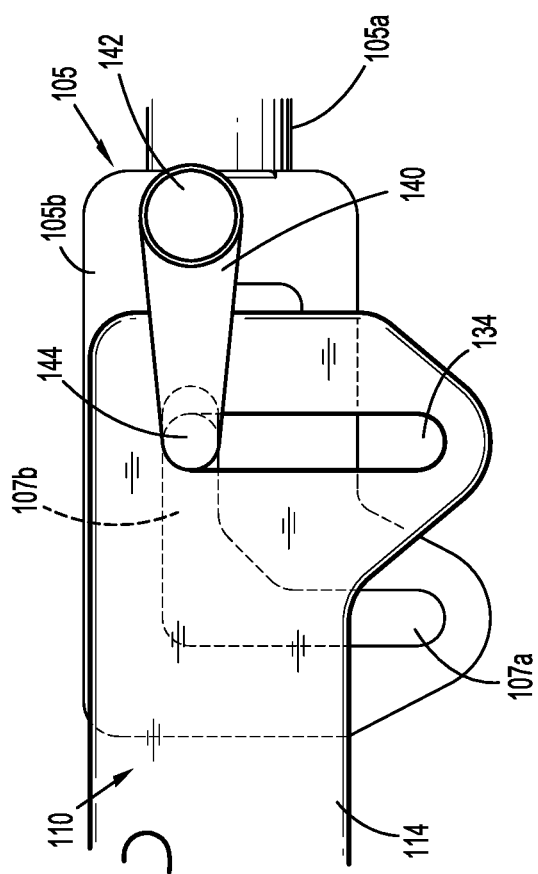
FIG. 13 is an enlarged view of the indicated area of detail shown in FIG. 12.

With reference to FIGS. 12 and 13, continued rotation of the first pivoting member 140, via continued advancement of the pusher 105, moves the protrusion 144a on the second ends 144 of the cam members 140a, 140b to the top ends of the vertical slots 134 to a position adjacent the horizontal portion 107b of the slot 107 of the pusher 105. In this position, further advancement of the pusher 105 will cause the protrusions 144a to move within the horizontal portions 107b of the slots 107 of the pusher 105 such that the cam members 140a, 140b will cease to rotate. As such, continued advancement of the pusher 105 will no longer effect advancement of the clamping plate assembly 110.

With reference to FIGS. 8 and 15-20, the alignment pin holder 180 of the loading unit 30 is configured to move the alignment pin 96 between retraced and advanced positions. The holder 180 defines a channel 188 along its length dimensioned to slidably receive the stapling plate 220 and includes a distal end 182, a proximal end 184, and a body 186 disposed between the distal and proximal ends 182, 184. The distal end 182 includes a vertically extending abutment member 191 that is configured to engage the proximal end 96a (FIG. 23) of the alignment pin 96 such that when the holder 180 is moved to an advanced position, the alignment pin 96 is advanced through the guide channel 94 (FIG. 7) of the cartridge 80, through the bore 104 of the cartridge 80, into the bore 56 (FIG. 19) of the anvil 52 and into the notch 58c of the stiffener plate 58. The body 186 of the holder 180 includes a pair of elongated slots 192a and 192b. The pins 132a, 132b (FIG. 20) extend through the slots 192a and 192b, respectively, to support the holder 180 for linear movement relative to the frame 36 and guide the holder 180 during movement of the holder 180 between the advanced and retracted positions.

Referring also to FIG. 14, the proximal end 184 of the holder 180 includes a capture member, such as, for example, a C-clip 194, that defines a vertical slot 196. The vertical slot 196 of the C-clip 194 of the holder 180 is configured to releasably receive a bar 214 of the second pivoting member 200. In addition, the L-shaped slots 136 of the clamp slide members 110a, 110b receive a cam member 212 of the second pivoting member 200, such that longitudinal movement of the clamp slide members 110a, 110b effect longitudinal movement of the holder 180, as will be described in detail below.

The second pivoting member 200 includes a pair of spaced apart sidewalls 202a, 202b each having a triangular configuration. In some embodiments, sidewalls 202a, 202b may assume a variety of configurations, such as, for example, oblong, tapered, squared, polygonal, kidney-bean shaped, or the like. Each sidewall 202a, 202b of the second pivoting member 200 has a first end 204, a second end 206, and an intermediate portion 208 disposed between the first and second ends 204, 206. The second end 206 has a pair of protrusions 210 extending laterally, outwardly from the sidewalls 202a, 202b. The protrusions 210 are configured to be pivotably received within the pivot holes 50 defined in the frame sides 44a, 44b to rotatably secure the second pivoting member 200 between frame sides 44a, 44b of the frame 36. The intermediate portion 208 of each sidewall 202a, 202b includes an inwardly extending cam member 212 configured to be received within the L-shaped slots 136 formed in the proximal end 114 of respective clamp slide members 110a, 110a of the clamping plate assembly 110. The first end 204 of the second pivoting member 200 has a link or bar 214 interconnecting the sidewalls 202a, 202b of the second pivoting member 200. The bar 214 is radially offset or spaced from the cam members 212 of the second pivoting member 200. As mentioned above, the bar 214 is releasably received within the vertical slot 196 of the C-clip 194 of the holder 180.

With reference again to FIGS. 15-20, advancement of the pusher 105 effects advancement of the clamp slide members 110a, 110b, as described above. In addition, advancement of the clamp slide members 110a, 110b effects rotation of the second pivoting member 200 and rotation of the second pivoting member 200 effects movement of the holder 180 between retracted and advanced positions. In particular, the L-shaped slot 136 of each clamp slide member 110a, 110b of the clamping plate assembly 110 includes a vertical portion 136a and a horizontal portion 136b. In the retracted position of the clamping plate assembly 110, the cam members 212 of the second pivoting member 200 are received within the vertical portion 136a of the slot 136 of each of the clamp slide members 110a 110b. As the clamping plate assembly 110 is advanced distally, via the pusher 105 and the first pivoting member 140 in the manner described above with reference to FIGS. 10-13, walls that define the vertical portion 136a of the L-shaped slot 136 of the clamping plate assembly 110 engage the cam members 212 of the second pivoting member 200 to pivot the second pivoting member 200, relative to the frame 36, about the second end 206 of the second pivoting member 200. As the second pivoting member 200 rotates, the bar 214 of the second pivoting member 200 engages the C-clip 194 of the holder 180 to urge the holder 180 in a distal direction, indicated by arrow "C" in FIG. 16. The bar 214 rides within the vertical slot 196 defined in the C-clip 194 as the bar 214 traverses an arced pathway.

Since the bar 214 of the second pivoting member 200 is radially distanced further from the protrusions 210 (i.e., the pivot point) of the second pivoting member 200 than the cam members 212, pivotal movement of the second pivoting member 200 effects movement of the bar 214 moves along its arced pathway at a greater rotational velocity than the cam members 212 move along their arced pathways. As such, the holder 180 is caused to advance distally relative to the clamping plate assembly 110 (i.e., the holder 180 advances relative to the frame 36 faster than the clamping plate assembly 110).

Figure 17:
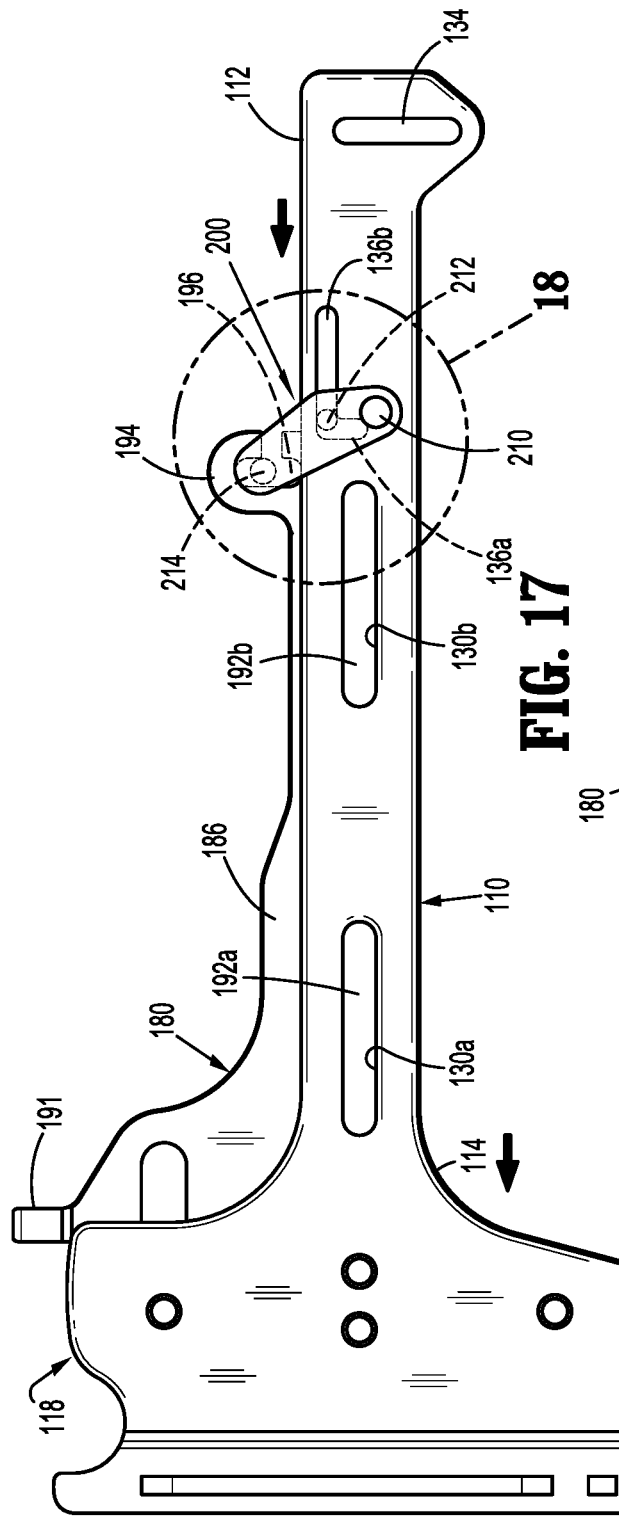
FIG. 17 is a side view of the loading unit of FIG. 3 with parts removed to illustrate the holder in a fully advanced position relative to the clamping plate assembly.
Figure 18:
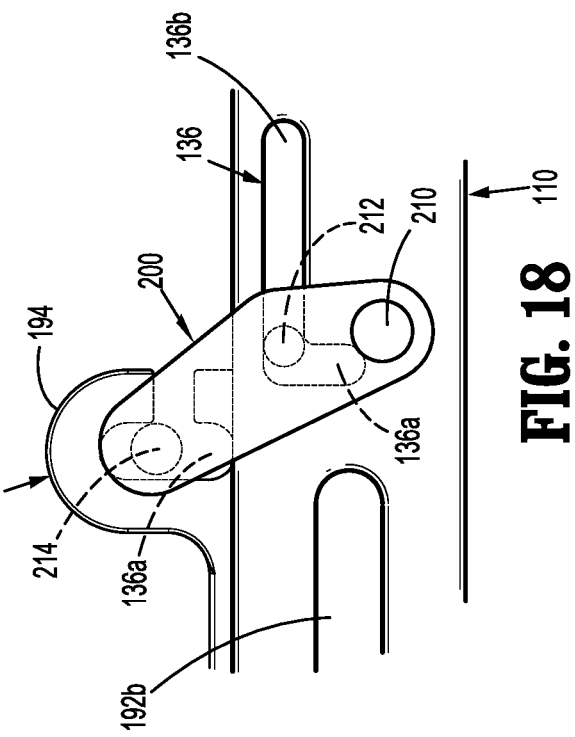
FIG. 18 is an enlarged view of the indicated area of detail shown in FIG. 17.
Figure 19:
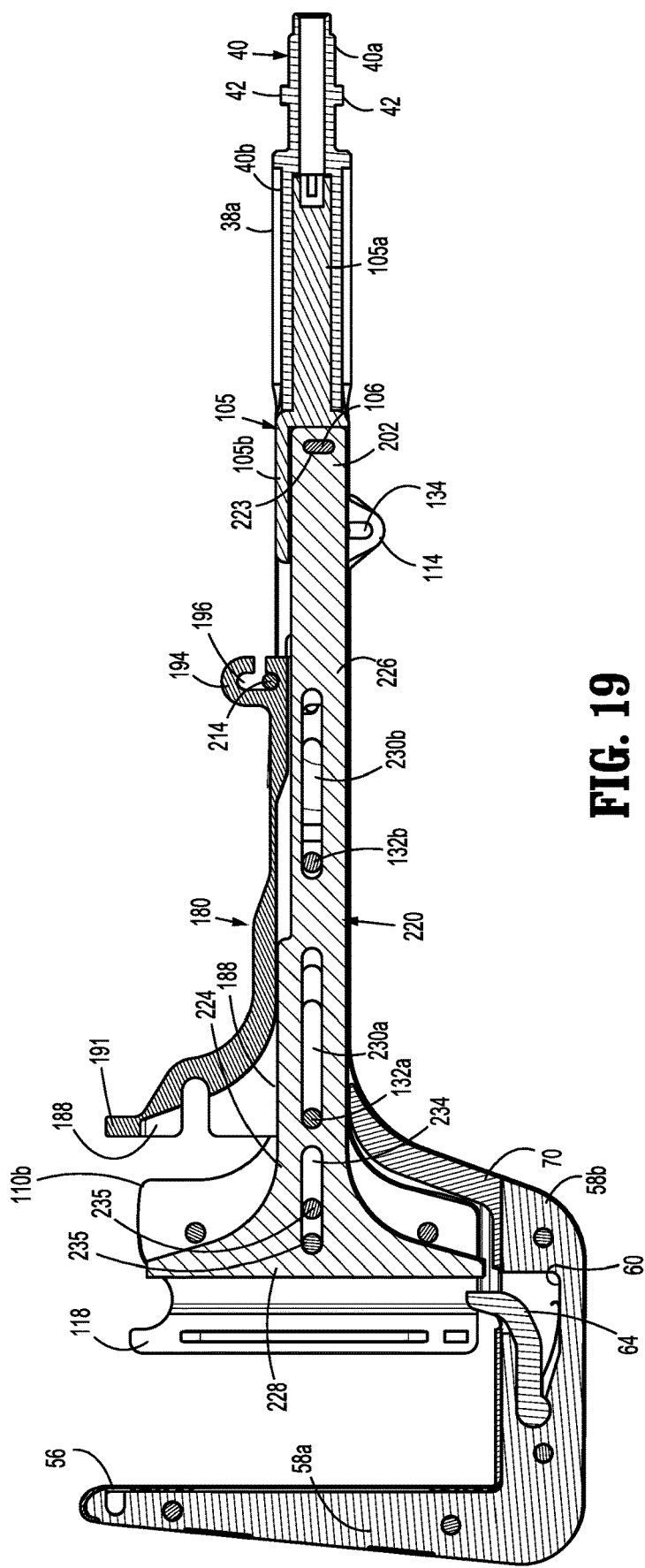
FIG. 19 is a cross-sectional view taken along section line 19-19 of FIG. 8.
Figure 20:
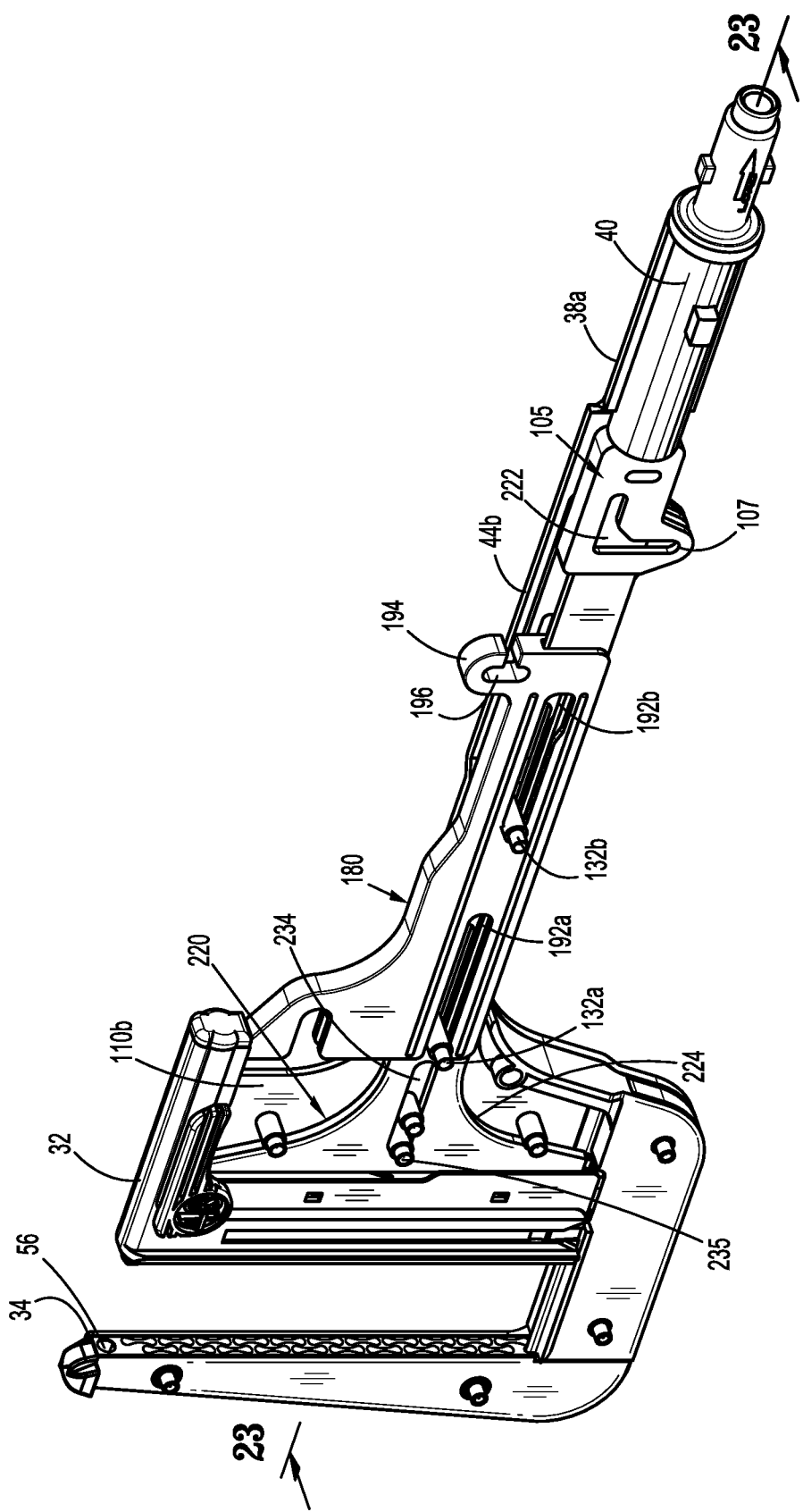
FIG. 20 is a perspective view of the loading unit of FIG. 3 with parts removed.
Figure 21:
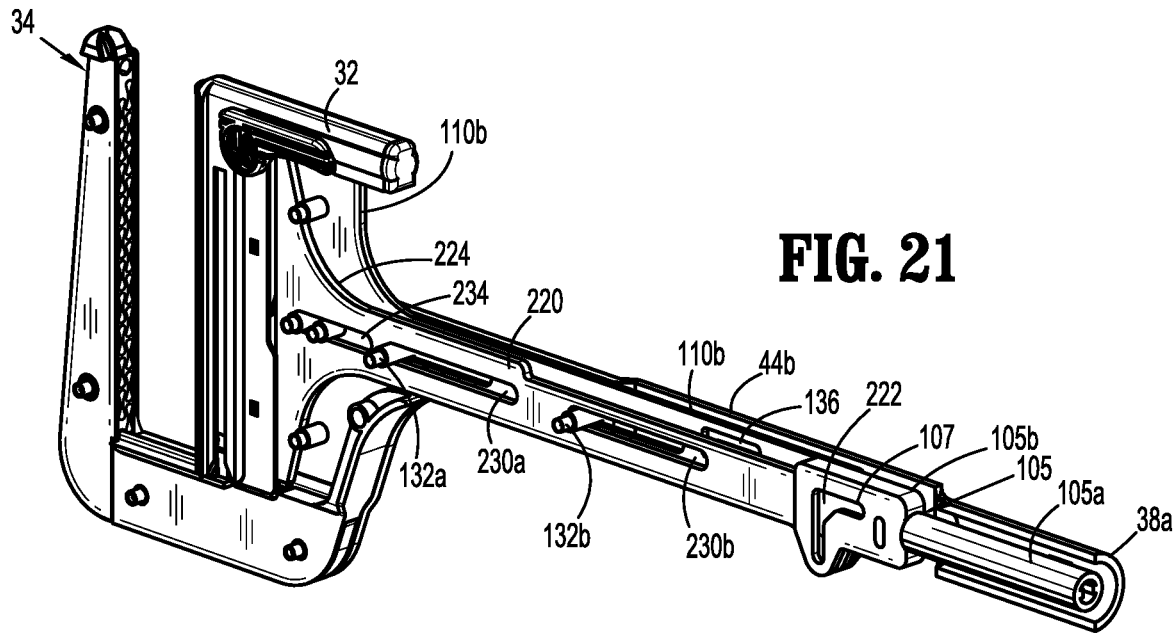
FIG. 21 is a perspective view of the loading unit of FIG. 20 with the holder removed.
Figure 22:
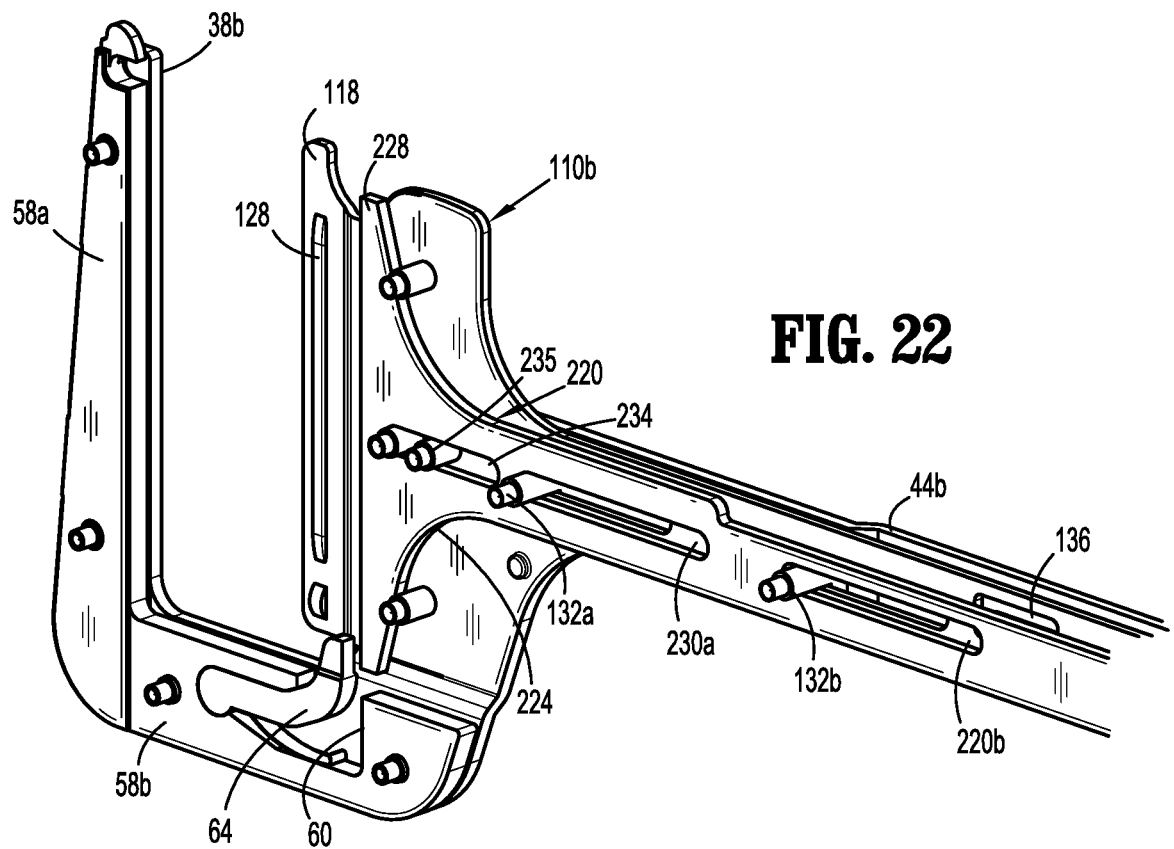
FIG. 22 is an enlarged view of the loading unit of FIG. 21 with the anvil and the cartridge assembly removed.

With reference to FIGS. 17 and 18, continued rotation of the second pivoting member 200, in response to continued advancement of the clamping plate assembly 110, moves the cam members 212 of the second pivoting member 200 to the top end of the vertical portion 136a of the L-shaped slots 136 to a position adjacent the horizontal portion 136b of the L-shaped slots. In this position, further rotation of the second pivoting member 200 will cause the cam members 212 to move within the horizontal portion 136b of the L-shaped slots 136 of the clamping plate assembly 110 such that the second pivoting member 200 will cease to rotate. As such, continued advancement of the clamping plate assembly 110 while the cam members 212 are positioned in the horizontal portion 136b of the L-shaped slots 136 will not effect advancement of the holder 180 and the clamping plate assembly 110 will advance distally relative to the holder 180.

With reference to FIGS. 19-22, the stapling plate 220 of the loading unit 100 is configured to eject the staples 91 from the cartridge assembly 32. The channel 188 (FIG. 8) defined longitudinally through the holder 180 slidably receives the stapling plate 220. The stapling plate 220 includes a proximal end 222, a distal end 224, and a body 226 disposed between the proximal and distal ends 222, 224. The proximal end 222 of the stapling plate 220 is fixedly disposed within the distal end 105b of the pusher 105 and has an opening 223 configured for receipt of the rivet or pin 106 of the pusher 105 to couple the proximal end 222 of the stapling plate 220 to the pusher 105. As such, longitudinal movement of the pusher 105 results in corresponding longitudinal movement of the stapling plate 220. In some embodiments, the stapling plate 220 may be connected to the pusher 105 via various fastening engagements, such as, for example, those alternatives described herein. The distal end 224 of the stapling plate 220 includes an engagement head 228 configured to engage the staple pushing members 90a, 90b (FIG. 7).

The body 126 of the stapling plate 220 includes a pair of elongated slots 230a, 230b dimensioned to slidably receive the pins 132a, 132b (FIG. 4). The slots 230a, 230b in the stapling plate 220 are longer than the slots 130a, 130b formed in the clamp slide members 110a, 110b, respectively. The increased length of the slots 230a, 230b permits the stapling plate 220 to be advanced distally, independently of the clamp slides 110a, 110b, through the cartridge assembly 32 to eject the staples 91 from the cartridge assembly 32.

The stapling plate 220 defines a forward elongated slot 234. The rivets 235 that extend between clamp slide members 110a, 110b to secure the clamp slide members 110a, 110b in spaced relation to each other extend through the slot 234. When the clamping plate assembly 110 is advanced from the retracted position to the advanced position, the rivets 235 engage the forward end of the slot 234 of the stapling plate 220 to concurrently advance the stapling plate 220 with the clamp slide members 110a, 110b. The slot 234 is of a length to allow the stapling plate 220 to continue to advance distally relative to the clamping plate assembly 110 upon the clamping plate assembly 110 reaching its fully advanced position. When the clamping plate assembly 110 reaches its fully advanced position, further advancement of the stapling plate 220 is effected by the pusher 105.

Figure 23:
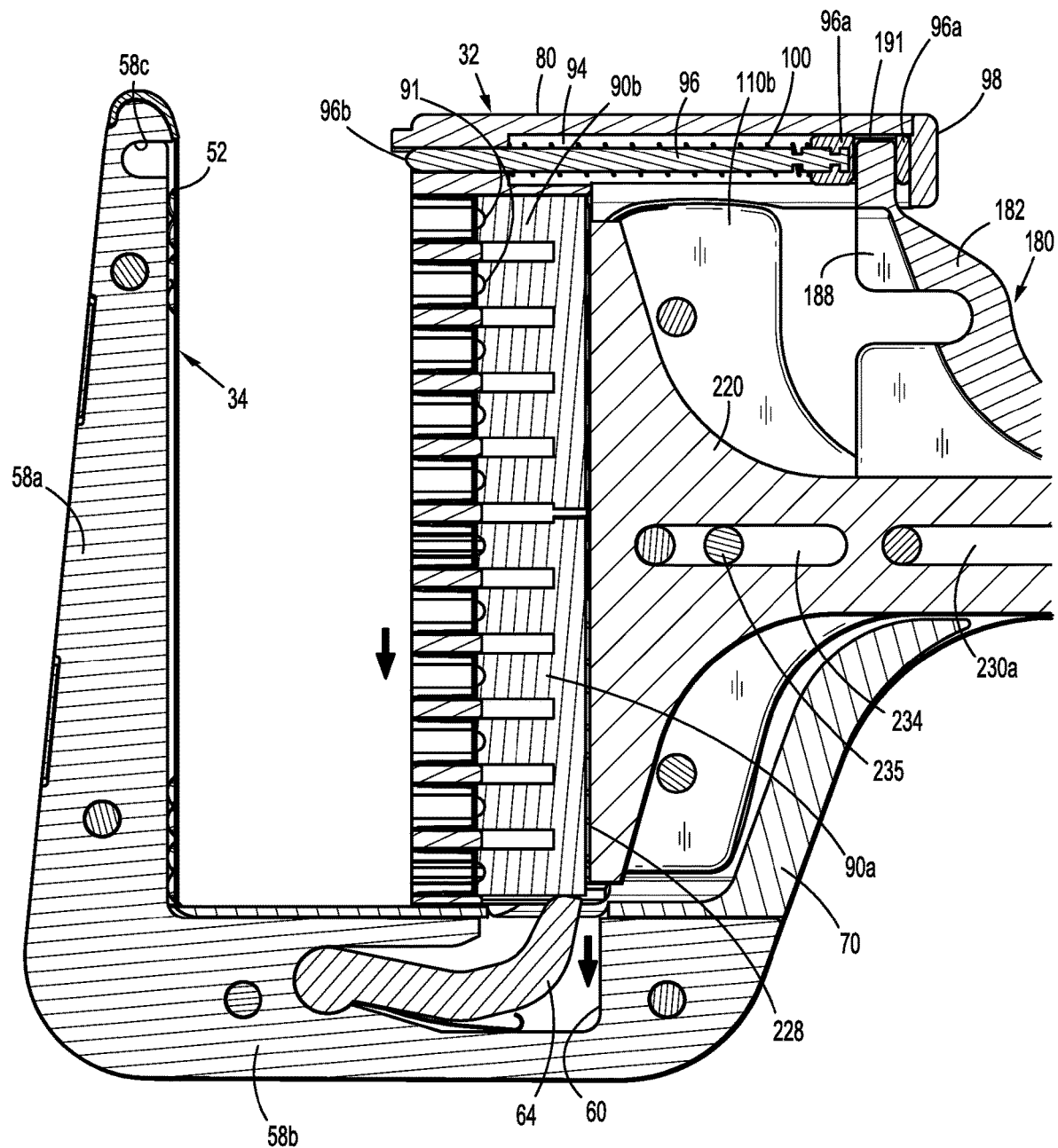
FIG. 23 is an enlarged, cross-sectional view taken along section line 23-23 of FIG. 20 with the clamping plate assembly, the holder, and the stapling plate in a retracted position.

Operation of the surgical stapling device 10 to effect stapling of tissue will now be described in detail with reference to FIGS. 23-25. FIG. 23 illustrates the distal end of the surgical stapling device 10 prior to use. The cartridge assembly 32 is inserted within the receptacle 126 defined between the clamp slide members 110a, 110b to engage and depress the interlock 64 as known in the art. With the interlock 64 depressed into the cutout 60, the interlock 64 no longer blocks movement of the stapling plate 220. With the trigger 17 (FIGS. 1 and 2) in the non-compressed position, the clamping plate assembly 110, the holder 180, and the stapling plate 220 are in their respective retracted positions. With the clamping plate assembly 110, the holder 180, and the stapling plate 220 in the retracted position, the associated cartridge 80, alignment pin 96, and staple pusher members 90a, 90b, respectively, are also in a retracted or non-actuated position. At this point, a clinician could optionally manually advance the holder 180 and, in turn, the alignment pin 96 by pushing thumb button(s) 24 (FIG. 1) distally. This operation would disengage the bar 214 of the second pivoting member 200 from the C-clip 194 of the holder 180 and advance the holder 180 distally independently of the clamp slide assembly 110.

Figure 24:
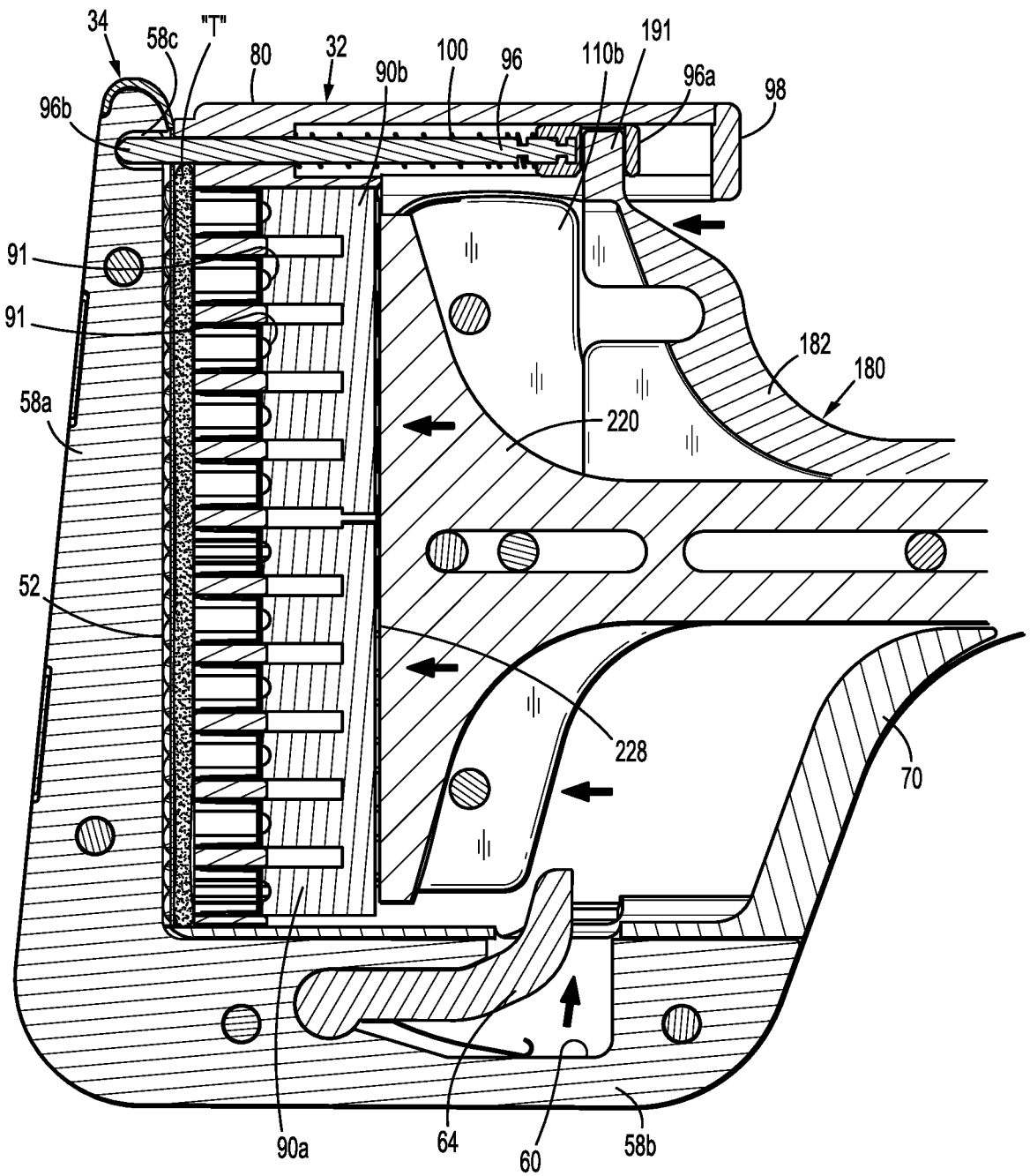
FIG. 24 illustrates the distal end of the loading unit shown in FIG. 23 with the clamping plate assembly and the holder in a fully advanced position to clamp and retain tissue, and the stapling plate in a partially advanced position.

FIG. 24 illustrates the surgical stapling device 10 after an initial approximation stroke of the trigger 17. Upon the trigger 17 being actuated, the drive shaft 23 (FIG. 1) of the adapter assembly 20 advances and, in turn, advances the pusher 105. Advancement of the pusher 105 effects advancement of the clamping plate assembly 110 via the first pivoting member 140 in the manner described above. Since the cartridge assembly 32 is connected to the head portion 118 of the clamping plate assembly 110 (see FIG. 8), advancement of the clamping plate assembly 110 also advances the cartridge assembly 32 including all of its components (e.g., the cartridge 80, the pusher assembly 90, and the alignment pin 96) toward the anvil assembly 34 to clamp tissue "T" disposed between the cartridge assembly 32 and the anvil assembly 34. During the initial approximation stroke, the stapling plate 220 moves with the clamping plate assembly 110 such that the associated staple pusher members 90a, 90b do not move relative to the cartridge 80.

Concurrently with the advancement of the clamping plate assembly 110 and the stapling plate 220, the holder 180 advances relative to the clamping plate assembly 110 via the second pivoting member 200 in the manner described above. Movement of the holder 180 from the retracted position to the advanced position urges the abutment member 191 of the holder 180 through the guide channel 94 of the cartridge 80 to advance the alignment pin 96 into the notch 58c of the anvil assembly 34 prior to the cartridge assembly 32 and the anvil assembly 34 being fully approximated. With the alignment pin 96 disposed in the notch 58c of the anvil assembly 34, tissue "T" disposed between the cartridge assembly 32 and the anvil assembly 34 is prevented from escaping the space between the cartridge assembly 32 and the anvil assembly 34.

Figure 25:
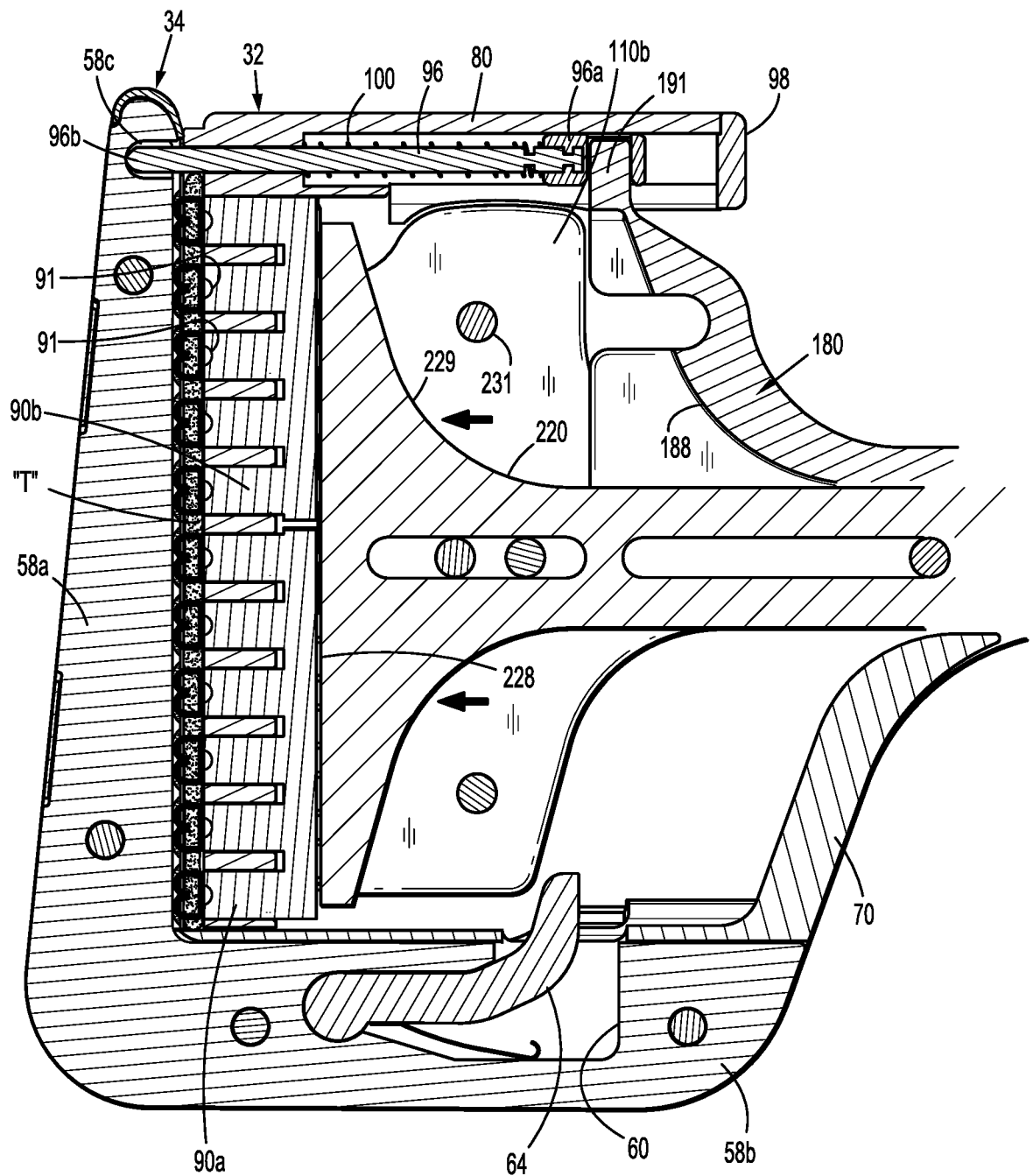
FIG. 25 illustrates the distal end of the loading unit shown in FIG. 23 with the stapling plate in a fully advanced position to effect stapling of tissue.

FIG. 25 illustrates the surgical stapling device 10 after the trigger 17 has been moved through the firing stroke to the fully actuated position. After the initial approximation stroke, continued actuation of the trigger 17 will cease to result in advancement of the clamping plate assembly 110 and its associated cartridge 80 due to the first pivoting member 140 no longer being pivoted by the pusher 105, as described in detail above with reference to FIGS. 12 and 13. Operating the firing stroke will continue to effect advancement of the stapling plate 220 due to the direct connection between the constantly moving pusher 105 and the stapling plate 220, as described in detail above. As the stapling plate 220 moves distally relative to the cartridge 80, the stapling plate 220 urges the staple pusher members 90a, 90b distally through the stationary cartridge 80 to eject the staples 91 from the cartridge assembly 32 into the tissue "T." This sequence of advancement of the cartridge 80, the alignment pin 96, and the staple pusher members 90a, 90b is effected by one continuous actuation of the trigger 17 due to the operative association of the pusher 105 with each of the clamping plate assembly 110, the holder 180, and the stapling plate 220.

The interlock 64 is normally urged by the pusher assembly 90 to a position located within the recess 60. After the cartridge assembly 32 has been fired, the pusher assembly 90 is no longer positioned to bias the interlock 64 into the recess 60. Until a new cartridge is inserted into the surgical stapling device 10, the interlock 64 will remain extended from the recess 60 to prevent the stapling plate 220 from being advanced distally.

After actuating the trigger, the trigger 17 will bias back toward the un-actuated position. As the trigger 17 returns to the un-actuated position, the clamping plate assembly 110 and its associated cartridge 80, the holder 180 and its associated alignment pin 96, and the stapling plate 220 and its associated staple pushing members 90a, 90b, all revert to their respective retracted positions via a similar sequence described above with respect to their respective advancements. In particular, with respect to FIG. 25, as the pusher 105 is moved from its advanced to its retracted position, in response to a decompressing of the trigger 17, the stapling plate 220 moves proximally due to being directly connected to the pusher 105. As the stapling plate 220 moves proximally, a proximally-oriented surface 229 of the engagement head 228 of the stapling plate engages a pin 231 extending laterally from the clamping plate assembly 110 to urge the clamping plate assembly 110 proximally. Proximal movement of the clamping plate assembly 110 effects proximal movement of the cartridge assembly 32, which is coupled to the clamping plate assembly 110.

With reference to FIGS. 15-18, continued proximal movement of the clamping plate assembly 110 causes the holder 180 to move proximally to its retracted position once the cam members 212 of the second pivoting member 200 move from the horizontal portion 136b of the L-shaped slot 136 of the clamping plate assembly 110 to the vertical portion 136a of the L-shaped slot 136 of the clamping plate assembly 110. With reference to FIGS. 10-13, continued proximal movement of the clamping plate assembly 110 also moves the second ends 144 of the first pivoting member 140 from the horizontal portion 107a of the slot 107 of the pusher 105 to the vertical portion 107a of the slot 107 of the pusher 105 to position the clamping plate assembly 110 in the retracted position. With the clamping plate assembly 110, the holder 180, and the stapling plate 220 in their respective retracted positions, another firing of the surgical stapling device 10 can be effected.

It will be understood that various modifications may be made to the embodiments disclosed herein. For example, the components of the surgical stapling device can be formed of any material suitable for surgical use and having the required strength characteristics. Therefore, the above description should not be construed as limiting, but merely as exemplifications of preferred embodiments. Those skilled in the art will envision other modifications within the scope and spirit of the claims appended hereto.

What is claimed is:
1. A surgical stapling device comprising:
 a frame having a proximal end and a distal end and defining a longitudinal axis;
 an anvil supported on the distal end of the frame;
 a pusher supported on the proximal end of the frame, the pusher being movable in relation to the frame between a fully retracted position and a fully advanced position;
 a clamping plate assembly supported by the frame, the clamping plate assembly having a proximal end and a distal end and being movable in relation to the frame between fully retracted and advanced positions;
 a cartridge supported on the distal end of the clamping plate assembly, the cartridge being movable in relation to the anvil between an unapproximated position and an approximated position in response to movement of the clamping plate assembly between its fully retracted and fully advanced positions, the cartridge including an alignment pin which is movable between a retracted position and an advanced position;

a holder supported on the frame, the holder being movable to effect movement of the alignment pin between its fully retracted and advanced positions;

a stapling plate supported by the frame, the stapling plate being movable between fully retracted and fully advanced positions to eject staples from the cartridge, wherein the pusher is operatively associated with the holder, the clamping plate assembly and the stapling plate such that longitudinal movement of the pusher along the longitudinal axis between its fully retracted and fully advanced positions effects longitudinal movement of the holder, the clamping plate assembly, and the stapling plate along the longitudinal axis between their respective fully retracted and fully advanced positions, wherein in its fully advanced position, the stapling plate ejects staples from the cartridge; and a handle assembly including a pivotable trigger coupled to the proximal end of the frame, wherein a single actuation of the pivotable trigger effects longitudinal movement of the pusher movement of the pusher from its fully retracted position to its fully advanced position.

2. The surgical stapling device according to claim 1, further comprising a first pivoting member including:
a first end pivotably coupled to the frame; and
a second end operatively coupled to the pusher and the clamping plate assembly such that the longitudinal movement of the pusher effects rotation of the first pivoting member to effect the longitudinal movement of the clamping plate assembly.

3. The surgical stapling device according to claim 2, wherein the proximal end of the clamping plate assembly defines a vertical slot, the second end of the first pivoting member riding along the vertical slot of the clamping plate assembly as the first pivoting member rotates relative to the frame.

4. The surgical stapling device according to claim 1, further comprising a second pivoting member including:
a first end operatively coupled to the holder;
a second end pivotably coupled to the frame; and
an intermediate portion operatively coupled to the clamping plate assembly such that the longitudinal movement of the clamping plate assembly via the longitudinal movement of the pusher rotates the second pivoting member to effect the longitudinal movement of the holder relative to the clamping plate assembly.

5. The surgical stapling device according to claim 4, wherein the clamping plate assembly defines a slot having a vertical portion and a horizontal portion, the intermediate portion of the second pivoting member being movable from a position in the vertical portion of the slot of the clamping plate assembly, in which the second pivoting member is rotatable relative to the frame in response to movement of the clamping plate assembly, to a position in the horizontal portion of the slot of the clamping plate assembly, in which the second pivoting member does not rotate relative to the frame in response to movement of the clamping plate assembly.

6. The surgical stapling device according to claim 5, wherein the second end of the second pivoting member is spaced from the intermediate portion of the second pivoting member.

7. The surgical stapling device according to claim 5, wherein the holder defines a vertical slot, the first end of the second pivoting member including a bar that rides along the vertical slot of the holder as the second pivoting member rotates relative to the frame.

8. The surgical stapling device according to claim 1, wherein the stapling plate is operatively associated with the pusher such that the longitudinal movement of the pusher results in the corresponding longitudinal movement of the stapling plate.

9. The surgical stapling device according to claim 1, further comprising a staple pushing member movably disposed adjacent the cartridge, the stapling plate being in abutment with the staple pushing member such that the staple pushing member moves longitudinally in response to longitudinal movement of the stapling plate.

10. The surgical stapling device according to claim 1, wherein the frame, the anvil, the pusher, the clamping plate assembly, the cartridge, the holder, and the stapling plate define a loading unit configured to be releasably coupled to the handle assembly.

11. A surgical stapling device, comprising a frame having a proximal end and a distal end and defining a longitudinal axis;
an anvil supported on the distal end of the frame;
a pusher supported on the proximal end of the frame, the pusher being movable in relation to the frame between a retracted position and an advanced position;
a clamping plate assembly supported by the frame, the clamping plate assembly having a proximal end and a distal end and being movable in relation to the frame between retracted and advanced positions;
a cartridge supported on the distal end of the clamping plate assembly, the cartridge being movable in relation to the anvil between an unapproximated position and an approximated position in response to movement of the clamping plate assembly between its retracted and advanced positions, the cartridge including an alignment pin which is movable between a retracted position and an advanced position;
a holder supported on the frame, the holder being movable to effect movement of the alignment pin between its retracted and advanced positions;
a stapling plate supported by the frame, the stapling plate being movable between retracted and advanced positions;
wherein the pusher is operatively associated with the holder, the clamping plate assembly and the stapling plate such that longitudinal movement of the pusher along the longitudinal axis between its retracted and advanced positions effects longitudinal movement of the holder, the clamping plate assembly, and the stapling plate along the longitudinal axis between their respective retracted and advanced positions;
further comprising a first pivoting member including:
a first end pivotably coupled to the frame; and
a second end operatively coupled to the pusher and the clamping plate assembly such that the longitudinal movement of the pusher effects rotation of the first pivoting member to effect the longitudinal movement of the clamping plate assembly; and
wherein the pusher defines a slot having a vertical portion and a horizontal portion, the second end of the first pivoting member being movable from the vertical portion, in which the first pivoting member is rotatable relative to the frame in response to movement of the pusher, to the horizontal portion, in which the first pivoting member is not rotatable relative to the frame in response to movement of the pusher.

12. A surgical stapling device comprising:
a frame having a proximal end and a distal end and defining a longitudinal axis;

a pusher supported on the proximal end of the frame, the pusher being movable in relation to the frame between a fully retracted position and a fully advanced position;

a clamping plate assembly supported by the frame, the clamping plate assembly having a proximal end and a distal end and being movable in relation to the frame between fully retracted and advanced positions to effect movement of a cartridge between a fully retracted position and a fully advanced position;

a holder supported on the frame, the holder being movable to effect movement of an alignment pin between a retracted position and an advanced position; and a stapling plate supported by the frame, the stapling plate being movable between fully retracted and advanced positions, wherein the pusher is operatively associated with the holder, the clamping plate assembly and the stapling plate such that longitudinal movement of the pusher along the longitudinal axis between its fully retracted and advanced positions effects movement of the holder, the clamping plate assembly, and the stapling plate along the longitudinal axis between their respective fully retracted and advanced positions, wherein in its fully advanced position, the stapling plate ejects staples from the cartridge;

a handle assembly including a pivotable trigger coupled to the proximal end of the frame, wherein a single actuation of the pivotable trigger effects longitudinal movement of the pusher from its fully retracted position to its fully advanced position.

13. The surgical stapling device according to claim 12, further comprising a first pivoting member including:
a first end pivotably coupled to the frame; and
a second end operatively coupled to the pusher and the clamping plate assembly such that the longitudinal movement of the pusher effects rotation of the first pivoting member to effect the longitudinal movement of the clamping plate assembly.

14. The surgical stapling device according to claim 13, wherein the proximal end of the clamping plate assembly defines a vertical slot, the second end of the first pivoting member riding along the vertical slot of the clamping plate assembly as the first pivoting member rotates relative to the frame.

15. The surgical stapling device according to claim 12, further comprising a second pivoting member including:
a first end operatively coupled to the holder;
a second end pivotably coupled to the frame; and
an intermediate portion operatively coupled to the clamping plate assembly such that the longitudinal movement of the clamping plate assembly via the longitudinal movement of the pusher rotates the second pivoting member to effect the longitudinal movement of the holder relative to the clamping plate assembly.

16. The surgical stapling device according to claim 15, wherein the clamping plate assembly defines a slot having a vertical portion and a horizontal portion, the intermediate portion of the second pivoting member being movable from a position in the vertical portion of the slot of the clamping plate assembly, in which the second pivoting member is rotatable relative to the frame in response to movement of the clamping plate assembly, to a position in the horizontal portion of the slot of the clamping plate assembly, in which the second pivoting member does not rotate relative to the frame in response to movement of the clamping plate assembly.

17. The surgical stapling device according to claim 16, wherein the second end of the second pivoting member is spaced from the intermediate portion of the second pivoting member.

18. The surgical stapling device according to claim 16, wherein the holder defines a vertical slot, the first end of the second pivoting member including a bar that rides along the vertical slot of the holder as the second pivoting member rotates relative to the frame.

19. The surgical stapling device according to claim 12, wherein the stapling plate is operatively associated with the pusher such that the longitudinal movement of the pusher results in the corresponding longitudinal movement of the stapling plate.

20. The surgical stapling device according to claim 12, further comprising a staple pushing member movably disposed adjacent the cartridge, the stapling plate being in abutment with the staple pushing member such that the staple pushing member moves longitudinally in response to longitudinal movement of the stapling plate.

21. A surgical stapling device comprising,
a frame having a proximal end and a distal end and defining a longitudinal axis;
a pusher supported on the proximal end of the frame, the pusher being movable in relation to the frame between a retracted position and an advanced position;
a clamping plate assembly supported by the frame, the clamping plate assembly having a proximal end and a distal end and being movable in relation to the frame between retracted and advanced positions to effect movement of a cartridge between a retracted position and an advanced position;
a holder supported on the frame, the holder being movable to effect movement of an alignment pin between a retracted position and an advanced position; and
a stapling plate supported by the frame, the stapling plate being movable between retracted and advanced positions,
wherein the pusher is operatively associated with the holder, the clamping plate assembly and the stapling plate such that longitudinal movement of the pusher along the longitudinal axis between its retracted and advanced positions effects movement of the holder, the clamping plate assembly, and the stapling plate along the longitudinal axis between their respective retracted and advanced positions;
further comprising a first pivoting member including:
a first end pivotably coupled to the frame; and
a second end operatively coupled to the pusher and the clamping plate assembly such that the longitudinal movement of the pusher effects rotation of the first pivoting member to effect the longitudinal movement of the clamping plate assembly;
wherein the pusher defines a slot having a vertical portion and a horizontal portion, the second end of the first pivoting member being movable from the vertical portion, in which the first pivoting member is rotatable relative to the frame in response to movement of the pusher, to the horizontal portion, in which the first pivoting member is not rotatable relative to the frame in response to movement of the pusher; and
a handle assembly including a pivotable trigger coupled to the proximal end of the frame, wherein a single actuation of the pivotable trigger effects longitudinal movement of the pusher between its retracted and advanced positions.

22. The surgical stapling device according to claim 21, wherein the frame, the pusher, the clamping plate assembly, the holder, and the stapling plate define a loading unit configured to be releasably coupled to the handle assembly.

* * * * *